(12) United States Patent
King et al.

(10) Patent No.: US 6,512,101 B1
(45) Date of Patent: Jan. 28, 2003

(54) BRANCHED HYDRAZONE LINKERS

(75) Inventors: Dalton King, Hamden, CT (US); Raymond A. Firestone, Ridgefield, CT (US); Pamela Trail, Yardley, PA (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/136,351

(22) Filed: Aug. 19, 1998

Related U.S. Application Data

(62) Division of application No. 08/770,614, filed on Dec. 19, 1996, now Pat. No. 5,824,805.
(60) Provisional application No. 60/009,100, filed on Dec. 22, 1995.
(51) Int. Cl.[7] ........................ C07H 17/02; C07H 17/00; C07H 15/04; C07H 15/12
(52) U.S. Cl. ...................................... 536/17.3; 536/17.4
(58) Field of Search ...................... 530/391.9; 536/17.3, 536/17.4

(56) References Cited

U.S. PATENT DOCUMENTS 4,112,217 A * 9/1978 Henry et al.
5,122,368 A * 6/1992 Greenfield et al.
5,965,106 A * 10/1999 Pomato et al.

FOREIGN PATENT DOCUMENTS

EP 294294 * 12/1988

OTHER PUBLICATIONS

A. Rosowsky et al, J. Med. Chem., vol. 24, No. 5, pp. 559–567 (1981).*

* cited by examiner

*Primary Examiner*—Mary E. Ceperley
(74) *Attorney, Agent, or Firm*—Keith R. Lange; Audrey F. Sher; Christopher A. Klein

(57) ABSTRACT

Branched hydrazone linkers for linking a targeting ligand such as an antibody to a therapeutically active drug. The point of branching is at a polyvalent atom and the number of drugs increases by a factor of two for each generation of branching. A preferred drug is doxorubicin.

9 Claims, 1 Drawing Sheet

BRANCHED HYDRAZONE LINKERS

CROSS-REFERENCE TO RELATED APPLICATION

This application is a divisional of Ser. No. 08/770,614, filed Dec. 19, 1996, which now U.S. Pat. No. 5,824,805 claims the benefit of U.S. Provisional Application No. 60/009,100 filed Dec. 22, 1995.

BACKGROUND OF THE INVENTION

Bifunctional compounds which link cytotoxic reagents to antibodies (i.e., "linkers") are known in the art. These compounds have been particularly useful in the formation of immunoconjugates directed against tumor associated antigens. Such immunoconjugates allow the selective delivery of toxic drugs to tumor cells. (See e.g., Hermentin and Seiler, "Investigations With Monoclonal Antibody Drug Conjugates," Behringer Insti. Mitl. 82:197–215 (1988); Gallego et al., "Preparation of Four Daunomycin-Monoclonal Antibody 791T/36 Conjugates With Anti-Tumor Activity," Int. J. Cancer 33:7737–44 (1984); Arnon et al., "In Vitro and In Vivo Efficacy of Conjugates of Daunomycin With Anti-Tumor Antibodies," Immunological Rev. 62:5–27 (1982).

Greenfield et al. have described the formation of acid-sensitive immunoconjugates containing the acylhydrazine compound, 3-(2-pyridyl-dithio)propionyl hydrazide conjugated via an acylhydrazone bond to the 13-keto position of an anthracycline molecule, and conjugation of this anthracycline derivative to an antibody molecule (Greenfield et al., European Patent Publication EP 0 328 147, published Aug. 16, 1989, which corresponds to pending U.S. Ser. No. 07/270,509, filed Nov. 16, 1988, now abandoned and U.S. Ser. No. 07/155,181, filed Feb. 11, 1988, now abandoned). This latter reference also discloses specific thioether-containing linkers and conjugates, including hydrazone thio-ether containing immunoconjugates.

Kaneko et al. (U.S. Ser. No. 07/522,996, filed May 14, 1990, now U.S. Pat. No. 5,137,877 which is equivalent to European Patent Publication, EP A 0 457 250, published Nov. 21, 1991) have also described the formation of conjugates containing anthracycline antibiotics attached to a bifunctional linker by an acylhydrazone bond at the C-13 position of an anthracycline molecule. In their invention the linkers contain a reactive pyridinyldithio- or an ortho-nitrophenyldithio-group, by which the linker reacts with a suitable group attached to a cell reactive ligand, to form the completed conjugate. An important consideration for immunoconjugates is that the relationship between drug potency and antigen expression must be appropriate in order to effect cytotoxicity on a broad range of malignant cells. Alterations in the potency of various immunoconjugates can be affected by changing the monoclonal antibody (MAb) utilized and/or the potency of the unconjugated drug. It is also possible to effect the potency of immunoconjugates by changes in the linker, both in terms of stability in circulation (Koizumi, M., K., Kunimatsu, M., Sakahara, H., Nakashima, T., Kawamura, Y., Watanabe, Y., Ohmomo, Y., Arano, Y., Yokoyama, A. and Torizuka, K. (1987), Preparation of $^{67}$Ga-labeled antibodies using deferoxamine as a bifunctional chelate. J. Immunol Methods 104, 93–102; Thorpe, P. E., Wallace, P. M., Knowless, P. P., Relf, M G., Brown, A. N. F., Watson, G. J. Knyba, R. E., Wawrzynczak, E. J. and Blakey, D. C. (1987), New coupling agents for the synthesis of immunotoxins containing a hindered disulfide bond with improved stability in vivo. Cancer Res. 47,5924–5931; Trail, P. A., Wilner, D., Lasch, S. J., Henderson, A. J., Greenfield, R. S., King, D., Zoeckler, M. E. and Braslawsky, G. R. (1992), Antigen specific activity of carcinoma reactive BR64-adriamycin conjugates evaluated in vitro and in human tumor xenograft modelsk, Cancer Research 52, 5693–5700; Trail, P. A., Willner, D., Lasch, S. J., Henderson, A. J., Hofstead, S. J., Casazza, A. M., Firestone R. A., Hellström, K. E. (1993), Cure of xenografted human carcinomas by BR96-Doxorubicin Immuno-conjugates, Science 261, 212–215; Trail, P. A., Willner, D. and Hellstrom, K. E. (1995), Site-directed delivery of anthracyclines for cancer therapy. Drug Development Research 34, 196–209) and in terms of drug/MAb molar ratio (Shih, L. B., Goldenberg, D. M., Xuan, H., Lu, H., Sharkey, R. M. and Hall, T. C. (1991), Anthracycline immunoconjugates prepared by a site specific linkage via an aminodextran intermediate carrier. International Journal of Cancer 41, 8320839; Trail et al.1992; Trail et al.,1995).

In particular, the in vitro potency of doxorubicin conjugates prepared with the internalizing anticarcinoma MAb BR64 and an acid labile hydrazone bond, was shown to increase as drug/MAb molar ratios increased from 1–8 (Trail et al.,1992; Trail et al.,1995). However, in these studies the increase in drug/MAb molar ratios was based on increasing the number of conjugation sites on the MAb which is self-limiting and has other drawbacks such as reduced antibody binding affinity.

In view of the above, it is clear that one of the problems in prior art immunoconjugates is the relatively low ratio of drug to targeting ligand (e.g., immunoglobulin) achievable. It would be highly desirable to have immunoconjugates which provide a higher ratio of drug to targeting ligand.

SUMMARY OF THE INVENTION

The present invention provides novel branched hydrazone linkers. The novel linkers are used to prepare novel drug/linker molecules and biologically active conjugates composed of a targeting ligand, a therapeutically active drug, and a branched linker capable of recognizing a selected target cell population (e.g., tumor cells) via the targeting ligand.

As used herein the term "drug/linker" or "linker/drug" molecule refers to the linker molecule coupled to two or more therapeutically active drug molecules, and the term "conjugate" refers to the drug/linker molecule coupled to the targeting ligand. The linkers are branched so that more than one drug molecule per linker are coupled to the ligand. The number of drugs attached to each linker varies by a factor of 2 for each generation of branching. Thus, the number of drug molecules per molecule of linker can be 2, 4, 8, 16, 32, 64, etc. The factor of branching can be expressed mathematically as $2^n$ wherein n is a positive integer. Thus, a singly branched linker will have a first generation of branching or $2^1$, i.e., contains two drug molecules per linker. A doubly branched linker will have a second generation of branching or $2^2$, i.e., contains four drug molecules per linker.

Thus, the present invention is directed to a branched linker for linking a thiol group derived from a targeting ligand to two or more drug moieties which comprises a compound having a terminus containing a thiol acceptor for binding to a thiol group (also called a sulfhydryl group) derived from a targeting ligand, at least one point of branching which is a polyvalent atom allowing for a level of branching of $2^n$ wherein n is a positive integer, and at least two other termini containing acylhydrazide groups capable of forming acylhyrdazone bonds with aldehyde or keto groups derived from a drug moiety. It is preferred that n is 1,2, 3, or 4; more preferably 1, 2 or 3; most preferably 1 or 2. It is also preferred that the polyvalent atom is carbon or nitrogen, and the targeting ligand is an antibody or fragment thereof.

As used in the preceeding paragraph, the phrase "thiol group derived from the targeting ligand" means that the thiol group is already present on the targeting ligand or that the targeting ligand is chemically modified to contain a thiol group, which modification optionally includes a thiol spacer group between the targeting ligand and the thiol group. Likewise, the phrase "an aldehyde or keto group derived from a drug moiety" means that the aldehyde or keto group is already present on the drug or the drug is chemically modified to contain an aldehyde or keto group.

Also provided by the invention are intermediates for preparing the linkers, drug/linkers and/or conjugates; and a method for treating or preventing a selected disease state which comprises administering to a patient a conjugate of the invention.

DETAILED DESCRIPTION OF THE INVENTION

Figure 1:
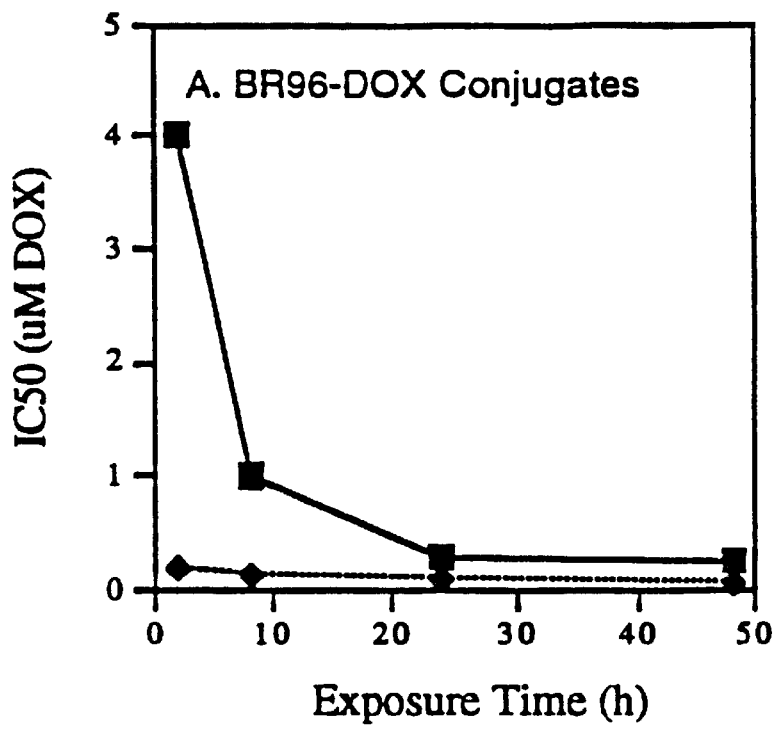
FIG. 1—In vitro potency of BR96 straight chains hydrazone and branched hydrazone conjugates following various exposure times as described in Example 62. —■— represents BR96 MCDOXHZN and ---◆--- represents BR96 MB-Glu-(DOX)$_2$.

According to the present invention the drug molecules are linked to the targeting ligand via the linker of the invention. The drug is attached to the linker through an acylhydrazone bond. The targeting ligand is attached to the linker through a thioether bond. The thioether bond is created by reaction of a sulfhydryl (thiol) group on the ligand, or on a short "thiol spacer" moiety attached to the ligand, with a thiol acceptor. The thiol acceptor can be a Michael Addition acceptor which becomes, after the reaction, a Michael Addition adduct. In a preferred embodiment, the targeting ligand is attached directly to the linker through a covalent thioether bond without a thiol spacer.

In a preferred embodiment the novel linker molecule of the invention has the formula

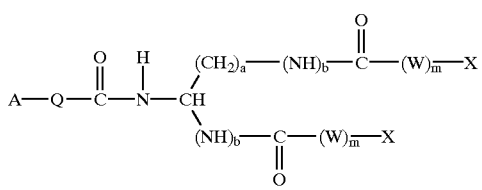

I wherein
A is a thiol acceptor;
Q is a bridging group;
b is an integer of 0 or 1;
W is a spacer moiety;
m is an integer of 0 or 1;
a is an integer of 2, 3 or 4; and X is a moiety of the formula —NH—NH$_2$ or

or a moiety of the formula

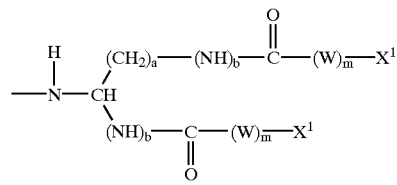

wherein

W, a, b and m are as defined hereinbefore, and
$X^1$ is a moiety of the formula —NH—NH$_2$ or

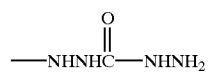

or a moiety of the formula

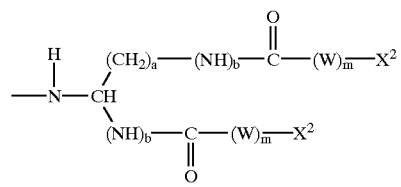

wherein

W, a, b, and m are defined hereinbefore, and
$X^2$ is a moiety of the formula NH—NH$_2$ or

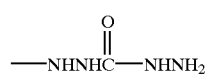

or a moiety of the formula

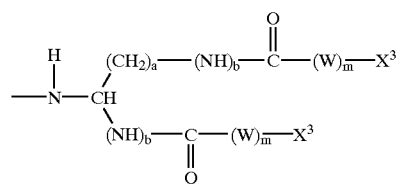

wherein

W, a, b, and m are as defined hereinbefore, and
$X^3$ is a moiety of the formula —NH—NH$_2$ or

or a moiety of the formula

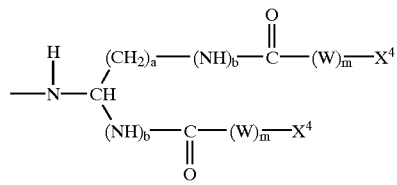

wherein

W, a, b and m are as defined hereinbefore, and
$X^4$ is a moiety of the formula —NH—NH$_2$ or

In another preferred embodiment the novel branched linker of the invention has the formula

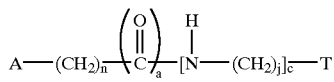   II wherein n is an integer of 1 to 6
a is an integer of 0 or 1,
j is an integer of 2 to 6,
c is an integer of 0 or 1,
provided that when a is 0, c must also be 0;
A is a thiol acceptor;
T is of the formula

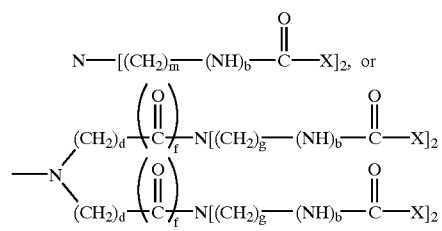

wherein
d is an integer of 2 to 6,
m is an integer of 1 or 2,
f is an integer of 0 or 1,
b is an integer of 0 or 1,
g is an integer of 1 or 2, and
X is a moiety of the formula —NH—NH$_2$ or

Preferred branched linkers of formula II are where d is 2, f is 0, g is 1, and/or b is 0.

Specific preferred compounds of formula II have the following formulae

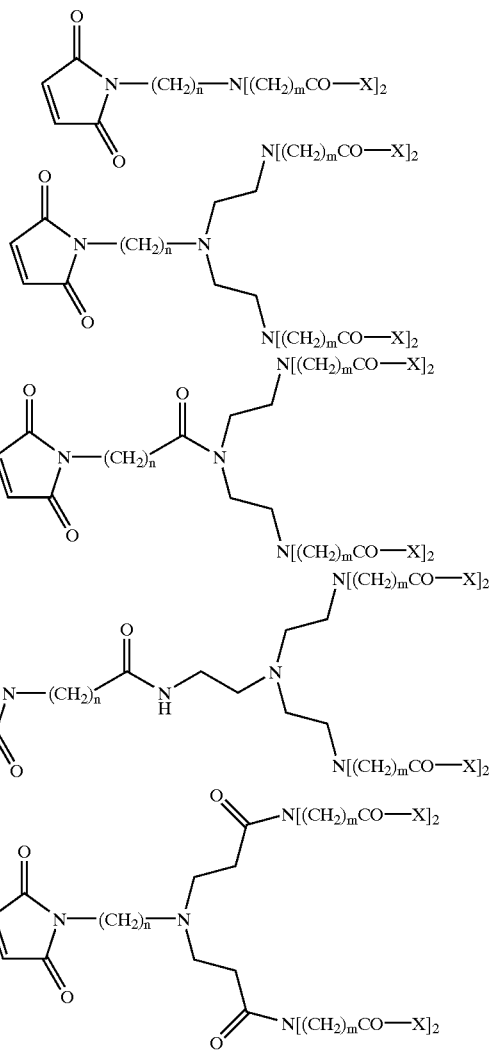

Preferred drug/linker molecules (alternatively referred to herein as "linker/drug" molecules) of the invention are when the X moieties of the compounds of formula I or II are of the formula —NH—N=Drug or

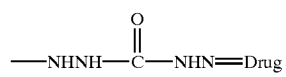

Preferred linker/drug molecules of the invention within the scope of formula I have the formulae

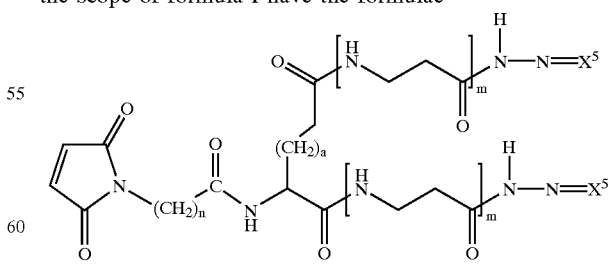

wherein
a is an integer of 0, 1, 2, or 3,
n is an integer of 1 to 6,
m is an integer of 0 or 1, and
$X^5$ is an anthracycline antibiotic;

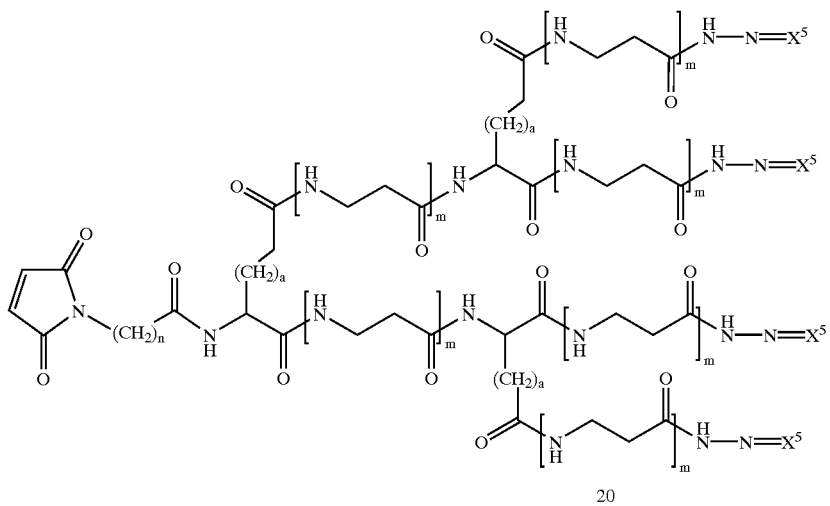

20 wherein
n is an integer of 1 to 6,
a is an integer of 0, 1, 2, or 3,
m is an integer of 0 or 1, and
$X^5$ is an anthracycline antibiotic;
Preferred novel conjugates prepared from the drug/linker molecules of the invention have the formula

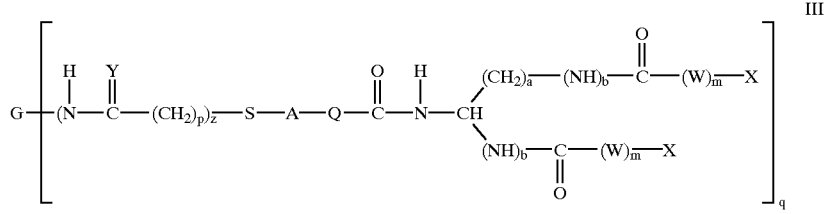

III wherein
A is a thiol adduct,
W is a spacer moiety,
Q is a bridging group,
m is an integer of 0 or 1,
a is an integer of 2, 3, or 4,
b is an integer of 0 or 1,
p is an integer of 1 to 6,
Y is O or $NH_2^+Cl^-$,
z is an integer of 0 or 1,
q is an integer of 1 to 10,
G is a targeting ligand, and
X is a moiety of the formula —NH—N=Drug or

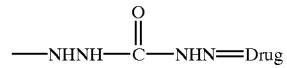

or a moiety of the formula

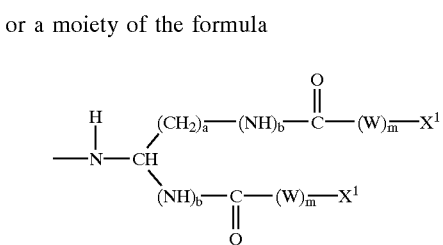

wherein W, a, b and m are as defined hereinbefore, and $X^1$ is a moiety of the formula —NH—N=Drug, or

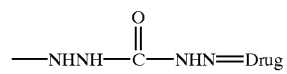

or a moiety of the formula

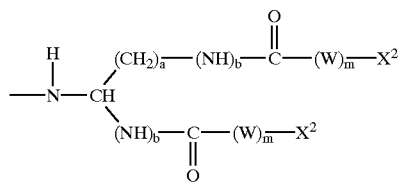

wherein W, a, b and m are as defined hereinbefore, and $X^2$ is a moiety of the formula —NH—N=Drug, or

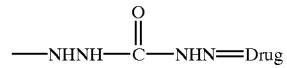

or a moiety of the formula

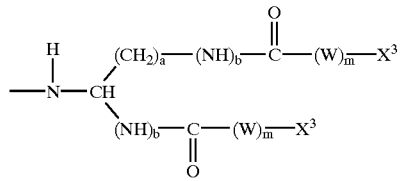

wherein
W, a, and m are defined hereinbefore, and
$X^3$ is a moiety of the formula —NH—N=Drug, or

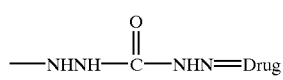

or a moiety of the formula

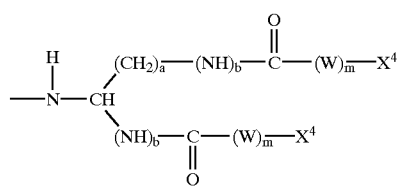

wherein
W a, b, and m are defined hereinbefore, and
$X^4$ is a moiety of the formula —NH—N=Drug or

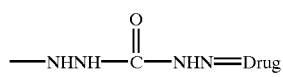

Other preferred novel conjugates of the invention have the formula

IV

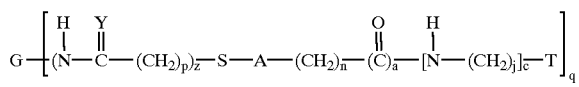

wherein
A is a thiol adduct,
n is an integer of 1 to 6,
a is an integer of 0 or 1,
j is an integer of 2 to 6,
c is an integer of 0 or 1,
p is an integer of 1 to 6,
Y is O or $NH_2^+Cl^-$,
z is an integer of 0 or 1,
q is an integer of 1 to 10,
G is a targeting ligand, and
T is of the formula

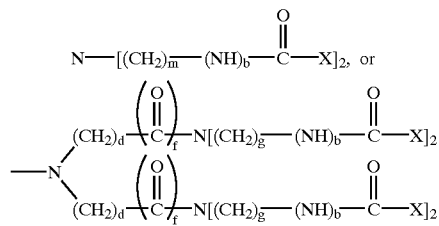

wherein
d is an integer of 2 to 6,
m is an integer of 1 or 2,
f is an integer of 0 or 1,
b is an integer of 0 or 1,
g is an integer of 1 or 2, and X is a moiety of the formula —NH—N=Drug or

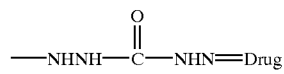

In one embodiment the drug moiety is an anthracycline antibiotic and the ligand is an antibody.

In a preferred embodiment the anthracycline is bound to the linker through an acylhydrazone bond at the 13-keto position of the anthracycline compound. The targeting ligand, preferably an antibody or fragment thereof, then is bound, through the linker, to the anthracycline compound. In an especially preferred embodiment, this linkage occurs through a reduced disulfide group (i.e. a free sulfhydryl or thiol group (—SH)) on an antibody).

In a most preferred embodiment the anthracycline drug moiety is adriamycin, the thiol acceptor ia a Michael Addition acceptor, from which the Michael Addition adduct is derived, especially a maleimido-group, and the antibody moiety is a chimeric or humanized antibody.

The conjugates of the invention retain both specificity and therapeutic drug activity for the treatment of a selected target cell population. They may be used in a pharmaceutical composition, such as one comprising a pharmaceutically effective amount of a compound of Formula III or IV associated with a pharmaceutically acceptable carrier, diluent or excipient.

The present invention provides novel branched linker/drug molecules composed of a drug, and a thioether-containing linker having at least two drug molecules which can be joined to a ligand capable of targeting a selected cell population. The drugs are joined to the linker through an acylhydrazone bond. The point of branching is a polyvalent atom, preferably a carbon atom or nitrogen atom. In a preferred embodiment, the ligand is joined directly to the linker through a thioether bond. Normally, this bond will be created by reaction of a reactive sulfhydryl (—SH) group on the ligand, or on a spacer moiety (e.g., one derived from the SPDP or iminothiolane chemistry described below), with a thiol acceptor such as a Michael Addition acceptor.

The invention also provides methods for the production of these drug conjugates and pharmaceutical compositions and methods for delivering the conjugates to target cells in which a modification in biological process is desired, such as in the treatment of diseases such as cancer, viral or other pathogenic infections, autoimmune disorders, or other disease states.

The conjugates comprise at least two drug molecules connected by a linker of the invention to a targeting ligand molecule that is reactive with the desired target cell population. The targeting ligand molecule can be an immunoreactive protein such as an antibody, or fragment thereof, a non-immunoreactive protein or peptide ligand such as bombesin or, a binding ligand recognizing a cell associated receptor such as a lectin or steroid molecule.

For a better understanding of the invention, the Drugs, the ligands and various components of the hydrazone linkers will be discussed individually.

The Spacer ("W")

As used herein, the term "spacer" refers to a bifunctional chemical moiety which is capable of covalently linking together two spaced chemical moieties into a stable tripartate molecule. Specifically, the "W" spacer links a keto group to a nitrogen atom. Examples of spacer molecules are described in S. S. Wong, *Chemistry of Protein Conjuaation* and *Crosslinking*, CRC Press, Florida, (1991); and G. E. Means and R. E. Feeney, *Bioconjugate Chemistry*, vol. 1, pp.2–12, (1990), the disclosures of which are incorporated herein by reference. Preferred spacers have the formula

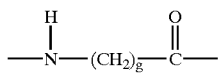

wherein g is an integer of 1 to 6, preferably 2 to 4, more preferably 2.

The most preferred spacer has the formula

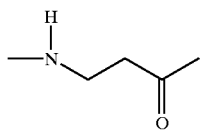

The Bridging Group ("Q")

The bridging group is a bifunctional chemical moiety which is capable of covalenting linking together two spaced chemical moieties into a stable tripartate molecule. Examples of bridging groups are described in S. S. Wong, *Chemistry of Protein Conjugation and Crosslinking*, CRC Press, Florida, (1991); and G. E. Means and R. E. Feeney, *Bioconjugate Chemistry*, vol. 1, pp.2–12, (1990), the disclosures of which are incorporated herein by reference. Specifically, the bridging group "Q", covalently links the thiol acceptor to a keto moiety. An example of a bridging group has the formula

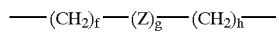

wherein
f is an integer of 0 to 10,
h is an integer of 0 to 10,
g is an integer of 0 or 1,
provided that when g is 0, then f+h is 1 to 10,
Z is S, O, NH, $SO_2$, phenyl, naphthyl, a cycloaliphatic hydrocarbon ring containing 3 to 10 carbon atoms, or a heteroaromatic hydrocarbon ring containing 3 to 6 carbon atoms and 1 or 2 heteroatoms selected from O, N, or S.

Preferred cycloaliphatic moieties include cyclopropyl, cyclobutyl, cyclopentyl, cyclohexyl, and the like. Preferred heteroaromatic moieties include pyridyl, furanyl, pyranyl, pyrimidinyl, pyrazinyl, pyridazinyl, oxazinyl, pyrrolyl, thiazolyl, morpholinyl, and the like.

In the bridging group it is preferred that when g is 0, f+h is an integer of 2 to 6 preferably 2 to 4 and more preferably 2. When g is 1, it is preferred that f is 0, 1 or 2, and that h is 0, 1 or 2.

The Thiol Acceptor

In the molecules of Formulas I, II, III, and IV, the thiol acceptor "A" is linked to the ligand via a sulfur atom derived from the ligand. The thiol acceptor becomes a thiol adduct after bonding to the ligand through a thiol group via a thioester bond. The thiol acceptor can be, for example, an alpha-substitited acetyl group. Such a group has the formula

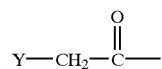

wherein Y is a leaving group. Examples of leaving groups include Cl, Br, I, meaylate, tosylate, and the like. If the thiol acceptor is an alpha-substituted acetyl group, the thiol adduct after linkage to the ligand forms the bond —S—$CH_2$—

Preferably, the thiol acceptor is a Michael Addition acceptor. A representative Michael Addition acceptor of this invention has the formula

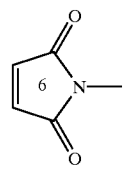

After linkage to the ligand, the Michael Addition acceptor becomes a Michael Addition adduct, such as of the formula A

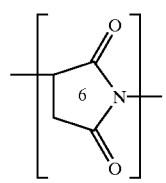

A

The Drug

The drug of the drug/linker molecule and conjugates of the present invention are effective for the usual purposes for which the corresponding drugs are effective, and have superior efficacy because of the ability, inherent in the ligand, to transport the drug to the desired cell where it is of particular benefit. Further, because the conjugates of the invention can be used for modifying a given biological response, the drug moiety is not to be construed as limited to classical chemical therapeutic agents.

The preferred drugs for use in the present invention are cytotoxic drugs, particularly those which are used for cancer therapy. Such drugs include, in general, DNA damaging agents, anti-metabolites, natural products and their analogs. Preferred classes of cytotoxic agents include the anthracycline family of drugs. Particularly useful members of that class include, for example, daunorubicin, doxorubicin, carminomycin, morpholino doxorubicin, diacetylpentyl doxorubicin and their analogues.

As noted previously, one skilled in the art may make chemical modifications to the desired compound in order to make reactions of that compound more convenient for purposes of preparing conjugates of the invention.

In the conjugate of Formula II, D is a drug moiety having pendant to the backbone thereof a chemically reactive functional group by means of which the drug backbone is bonded to the linker, said functional group selected from the group consisting of an aldehyde or a ketone.

A highly preferred group of cytotoxic agents for use as drugs in the present invention include drugs of the following formula:

The Anthracyclines Antibiotics Of Formula (V)

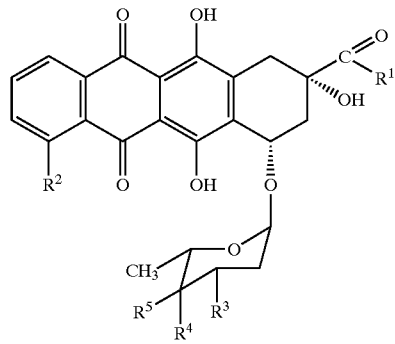

(V)

wherein
$R^1$ is —$CH_3$, —$CH_2OH$, —$CH_2OCO(CH_2)_3CH_3$ or —$CH_2OCOCH(OC_2H_5)_2$ $R^2$ is —$OCH_3$, —OH or —H $R^3$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethylamine, 1-cyano-2-methoxyethyl amine, or NH—$(CH_2)_4$—CH$(OAc)_2$;

$R^4$ is —OH, —OTHP, or —H; and $R^5$ is —OH or —H provided that $R^5$ is not —OH when $R^4$ is —OH or —OTHP.

One skilled in the art understands that structural Formula (V) includes compounds which are drugs, or are derivatives of drugs, which have acquired in the art different generic or trivial names. Table I, which follows, represents a number of anthracycline drugs and their generic or trivial names and which are especially preferred for use in the present invention.

Of the compounds shown in Table I, the most highly preferred drug is Doxorubicin. Doxorubicin (also referred to herein as "DOX") is that anthracycline shown on Table I in which $R^1$ is —$CH_2OH$, $R^3$ is —$OCH_3$, $R^4$ is —$NH_2$, $R^5$ is —OH, and $R^6$ is —H.

TABLE I

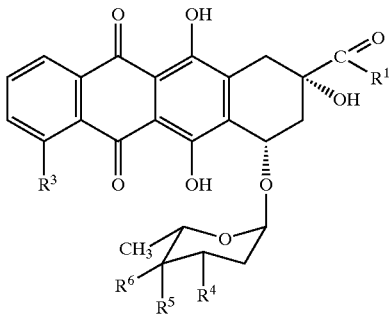

| Compound | $R^1$ | $R^3$ | $R^4$ | $R^5$ | $R^6$ |
|---|---|---|---|---|---|
| Daunorubicin[a] | $CH_3$ | $OCH_3$ | $NH_2$ | OH | H |
| Doxorubicin | $CH_2OH$ | $OCH_3$ | $NH_2$ | OH | H |
| Detorubicin | $CH_2OCOCH(OC_2H_5)_2$ | $OCH_3$ | $NH_2$ | OH | H |
| Carminomycin | $CH_3$ | OH | $NH_2$ | OH | H |
| Idarubicin | $CH_3$ | H | $NH_2$ | OH | H |
| Epirubicin | $CH_2OH$ | $OCH_3$ | $NH_2$ | H | OH |
| Esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |
| Morpholino-Dox | $CH_2OH$ | $OCH_3$ | 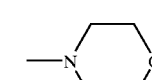 | OH | H |
| Cyano-morpholino-Dox | $CH_2OH$ | $OCH_3$ | 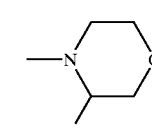 | OH | H |
| DAPDox | $CH_2OH$ | $OCH_3$ | —$NH(CH_2)_4CH(OAc)_2$ | OH | H |

[a]"Daunomycin" is an alternate name for daunorubicin

The Targeting Ligand

The "ligand" includes within its scope any molecule that specifically binds or reactively associates or complexes with a receptor or other receptive moiety associated with a given target cell population. This cell reactive molecule, to which the drug reagent is linked via the linker in the conjugate, can be any molecule that binds to, complexes with or reacts with the cell population sought to be therapeutically or otherwise biologically modified and, which possesses a free reactive sulfhydryl (—SH) group or can be modified to contain such a sulfhydryl group. The cell reactive molecule acts to deliver the therapeutically active drug moiety to the particular target cell population with which the ligand reacts. Such molecules include, but are not limited to, large molecular weight proteins such as, for example, antibodies, smaller molecular weight proteins, polypeptides or peptide ligands, and non-peptidyl ligands.

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-a and TGF-b, vaccinia growth factor ("VGF"), insulin and insulin-like growth factors I and II. Non-peptidyl ligands may include, for example, carbohydrates, lectins, and apoprotein from low density lipoprotein.

The immunoreactive ligands comprise in antigen-recognizing immunoglobulin (also referred to as "antibody"), or an antigen-recognizing fragment thereof. Particularly preferred immunoglobulins are those immunoglobulins which can recognize a tumor-associated antigen. As used, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobuin can be derived from any species. Preferably, however, the immunoglobulin is of human, murine, or rabbit origin. Furthermore, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments may include, for example, the Fab', F(ab')$_2$, F$_v$ or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, *J. Immunology*, 131, 2895 (1983); Lamoyi et al., *J. Immunological Methods*, 56, 235 (1983); Parham, id., 53, 133 (1982); and Matthew et al., id., 50, 239 (1982).

The immunoglobulin can be a "chimeric antibody" as that term is recognized in the art. Also the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or more or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT Application WO83/03679, published Oct. 27, 1983, and published European Application EPA 0 217 577, published Apr. 8, 1987, both of which are incorporated herein by reference. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art.

In addition the immunoglobulin may be a single chain antibody ("SCA"). These may consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dabs) which possess antigen-binding activity. See, e.g., G. Winter and C. Milstein, *Nature*, 349, 295 (1991); R. Glockshuber et al., *Biochemistry* 29, 1362 (1990); and E. S. Ward et al., *Nature* 341, 544 (1989).

Especially preferred for use in the present invention are chimeric monoclonal antibodies, preferably those chimeric antibodies having specificity toward a tumor associated antigen. As used herein, the term "chimeric antibody" refers to a monoclonal antibody comprising a variable region, i.e., binding region, from one source or species and at least a portion of a constant region derived from a difference source of species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immungobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L., et al., *Proc. Nat'lAcad. Sci*, 81 6851 (1984).

Encompassed by the term "chimeric antibody" is the concept of "humanized antibody", that is those antibodies in which the framework or "complementarity determining regions ("CDR") have been modified to comprise the CDR of an immunoglobulin of different specificitry as compared to that of the parent immunoglobulin. In a preferred embodiment, a murine CDR is grafted into the framework region of a human antibody to prepare the "humanized antibody". See, e.g., L. Riechmann et al., *Nature* 332, 323 (1988); M. S. Neuberger et al., *Nature* 314, 268 (1985). Particularly preferred CDR's correspond to those representing sequences recognizing the antigens noted above for the chimeric and bifunctional antibodies. The reader is referred to the teaching of EPA 0 239 400 (published Sep. 30, 1987), incorporated herein by reference, for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, WO86/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, Md. 20852 or, commercially, for example, from Boehringer-Mannheim Biochemicals, P.O. Box 50816, Indianapolis, Ind. 46250.

Particularly preferred monoclonal antibodies for use in the present invention are those which recognize tumor associated antigens. Such monoclonal antibodies, are not to be so limited, however, and may include, for example, the following (the disclosures of which are incorporated herein by reference):

| Antigen Site Recognized | Monoclonal Antibodies | Reference |
|---|---|---|
| Lung Tumors | KS1/4 | N. M. Varki et al., Cancer Res. 44:681, 1984. |
| | 534,F8;604A9 | F. Cuttitta et al., in G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45:3274, 1985. |
| Small Cell Lung Cancer | TFS-2 | Okabe et al., Cancer Res., 45:1930, 1985. |
| Colon Cancer | 11.285.14 14.95.55 | G. Rowland et al., Cancer Immunol. Immunother., 19:1, 1985. |
| | NS-3a-22,NS-10 NS-19-9,NS-33a NS-52a,17-1A | Z. Steplewski et al., Cancer Res., 41:2723, 1981. |
| Carcino-embryonic | MoAb 35 or ZCE025 | Acolla, R. S. et al., Proc. Nat. Acad. Sci., (USA), 77:563, 1980. |
| Melanoma | 9.2.27 | T. F. Bumol and R. A. Reiseld, Proc. Natl. Acad. Sci., (USA), 79:1245, 1982. |
| p97 | 96.5 | K. E. Hellstrom et al., Monoclonal Antibodies and Cancer, loc. cit. p. 31. |
| Antigen T65 | T101 | Boehringer-Mannheim P.O. Box 50816 Indianapolis, IN 46250 |
| Ferritin | Antiferrin | Boehringer-Mannheim P.O. Box 50816 Indianapolis, IN 46250 |
| | R24 | W. G. Dippold et al., Proc. Natl. Acad. Sci. (USA), 77:6114, 1980. |
| Neuroblastoma | P1 153/3 | R. H. Kennet and F. Gilbert, Science, 203:1120, 1979. |
| | MIN 1 | J. T. Kemshead in Monoclonal Antibodies and Cancer, loc. cit. p. 49. |
| | UJ13A | Goldman et al., Pediatrics, 105:252, 1984. |
| Glioma | BF7, GE2, CG12 | N. de Tribolet et al., in Monoclonal Antibodies and Cancer, loc. cit. p. 81. |
| Ganglioside | L6 | I. Hellstrom et al., Proc. Natl. Acad. Sci. (USA), 83:7059 (1986); U.S. Pat. Nos. 4.906,562, issued Mar. 6, 1990 and 4,935,495, issued Jun. 19, 1990. |
| | Chimeric L6 | U.S. Ser. No. 07/923,244, filed Oct. 27, 1986, equivalent to PCT Patent Publication, wo 88/03145, published May 5, 1988. |
| Lewis Y | BR64 | U.S. Ser. No. 07/289,635, filed Dec. 22, 1988, and U.S. Ser. No. 07/443,696, filed Nov. 29, 1989, equivalent to European Patent Publication, EP A 0 375 562, published Jun. 27, 1990. |
| fucosylated Lewis Y | BR96, Chimeric BR96 | U.S. Ser. No. 07/374,947, filed Jun. 30, 1989, and U.S. Ser. No. 07/544,246, filed Jun. 26, 1990, equivalent to PCT Patent Publication, WO 91/00295, published Jan. 10, 1991. |
| Breast Cancer | B6.2, B72.3 | D. Colcher et al., in Monoclonal Antibodies and Cancer, loc. cit. p. 121. |

-continued

| Antigen Site Recognized | Monoclonal Antibodies | Reference |
|---|---|---|
| Osteogenic Sarcoma | 791T/48, 791T/36 | M. J. Embleton, ibid, p. 181. |
| Leukemia | CALL 2 | C. T. Teng et al., Lancet, 1.01, 1982. |
| | anti-idiotype | R.A. Miller et al., N. Engl. J. Med., 306:517, 1982. |
| Ovarian Cancer | OC 125 | R. C. Bast et al., J. Clin. Invest., 68:1331, 1981. |
| Prostate Cancer | D83.21, P6.2, Turp-27 | J. J. starling et al., in Monoclonal Antibodies and Cancer, loc. cit, p. 253. |
| Renal Cancer | A6H, D5D | P. H. Lange et al., Surgery, 98:143, 1985. |

In a preferred embodiment, the ligand containing conjugate is derived from chimeric antibody BR96, "ChiBR96", disclosed in U.S. Ser. No. 07/544,246, filed Jun. 26, 1990, and which is equivalent to PCT Published Application, WO 91/00295, published Jan. 10, 1991; the disclosures of which are incorporated herein by reference. ChiBR96 is an internalizing murine/human chimeric antibody and is reactive, ad noted, with the fucosylated Lewis Y antigen expressed by human carcinoma cells such as those derived from breast, lung, colon, and ovarian carcinomas. Modified and/or humanized BR96 antibody can also be used in the present invention; examples of such anitbodies are disclosed in U.S. Ser. No. 08/285,936, filed Aug. 4, 1994, and U.S. Ser. No. 08/487,860, filed Jun. 7, 1995; the disclosures of which are incorporated herein by reference. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC 10460. ChiBR96 is derived, in part, from its source parent, BR96. The hybridoma expressing BR96 was deposited, on Feb. 21, 1989, at the ATCC, under the terms of the Budapest Treaty and is available under the accession number HB 10036. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

Thus, as used "immunoglobulin" or "antibody" encompasses within its meaning all of the immunoglobulin/antibody forms or constructions noted above.

The conjugates of the invention demonstrate improved activity relative to linear conjugates. The present invention also encompasses pharmaceutical compositions, combinations and methods for treating diseases such as cancers and other tumors, non-cytocidal viral or other pathogenic infections, and auto-immune diseases. More particularly, the invention includes methods for treating disease in mammals wherein a pharmaceutically effective amount of at least one conjugate of the invention is administered in a pharmaceutically acceptable manner to the host mammal, preferably humans.

Alternative embodiments of the methods of the invention include the administration, either simultaneously or sequentially, of a number of different conjugates, i.e., bearing different drugs or different targeting ligands, for use in methods of combination chemotherapy. For example, an embodiment of this invention may involve the use of a number of conjugates wherein the specificity of the antibody component of the conjugate varies, i.e., a number of conjugates are used, each one having an antibody that binds specifically to a different antigen or to different sites or epitopes on the same antigen or to different sites or epitopes on the same antigen present on the cell population of interest. The drug component of these conjugates may be the same or may vary. For example, this embodiment may be especially useful in the treatment of certain tumors where the amounts of the various antigens on the surface of a tumor is unknown or the tumor cell population is heterogeneous in antigen expression and one wants to be certain that a sufficient amount of drug is targeted to all of the tumor cells at the tumor site. The use of a number of conjugates bearing different antigenic or epitope specificities for the tumor increases the likelihood of obtaining sufficient drug at the tumor site. Additionally, this embodiment is important for achieving a high degree of specificity for the tumor because the likelihood that normal tissue will possess all of the same tumor-associated antigens is small (see, J. Immunol., 127(1), pp. 157–60 (1981)).

Alternatively, a number of different conjugates can be used, wherein only to drug component of the conjugate varies. For example, a particular antibody can be linked to two or more doxorubicins to form one conjugate and can be linked to two or more daunomycins to form a second conjugate. Both conjugates can then be administered to a host to be treated and will localize, due to the antibody specificity, at the site of the selected cell population sought to be eliminated. Both drugs will then be released at that site. This embodiment may be important where there is some uncertainty as to the drug resistance of a particular cell population such as a tumor because this method allows the release of a number of different drugs at the site of or within the target cells. An additional embodiment includes the conjugation of more than one drug to a particular antibody to form a conjugate bearing a variety of different drugs along its surface—all linked to the antibody via acylhydrazone bonds. Administration of the conjugate of this embodiment results in the release of a number of different drugs at the site of or within the target cells. Furthermore, a combination of drug-targeting ligand conjugates can be used wherein the drug can be targeted to a cell population carrying a specific antigen as well as a receptor for a specific ligand on its surface. Again, one type of drug or number of different drugs can be used in this combination therapy.

The conjugates of the invention can be administered in the form of pharmaceutical compositions using conventional modes of administration including, but not limited to, intravenous, intraperitoneal, oral, intralymphatic, or administration directly into the site of a selected cell population such as a tumor. Intravenous administration is preferred. In the case of the conjugates, for in vivo treatment, it may be useful to use conjugates comprising antibody fragments such as Fab or F(ab")$_2$ or chimeric or humanized antibodies.

The pharmaceutical compositions of the invention-comprising the conjugates—may be in a variety of dosage forms which include, but are not limited to, solid, semi-solid and liquid dosage forms such as tablets, pills, powders, liquid solutions or suspensions, suppositories, polymeric microcapsules or microvesicles, liposomes, and injectable or infusible solutions. The preferred form depends upon the mode of administration and the therapeutic application.

The pharmaceutical compositions may also include conventional pharmaceutically carriers known in the art such as serum proteins such as human serum albumin, buffer substances such as phosphates, water or salts or electrolytes.

The most effective mode of administration and dosage regimen for the conjugates of this invention depends upon the severity and course of the disease, the patient's health and response to treatment and the judgment of the treating physician. Accordingly, the dosages of the conjugates and any accompanying compounds should be titrated to the individual patient. Nevertheless, an effective dose of the conjugates may be in the range of from about 1 to about 100 mg/m$^2$ drug or from about 500–5000 mg/m$^2$ antibody. An effective dose of the conjugates containing ligands other than antibodies may be in the range of from about 1 to about 100 mg/m$^2$ drug or from about 1 to about 100 mg/m$^2$ ligand.

Preparation of the Molecules of the Invention

The carbon-branched linker is derived from a bis-carboxylic acid, which also contains a protected amine functionality. Through a multi-step process, the carboxylic acid groups are converted to terminal hydrazide groups, whereby the amino group is elaborated to yield a terminal thiol acceptor. Condensation of the multiple hydrazide with a drug containing an aldehyde or ketone groups yields a multiple acylhydrazone of the drug.

The nitrogen-branched linker is derived from an oligoamine, differentially protected in such a way that all but one amino group are elaborated to yield terminal N, N-dialkanoylhydrazide groups. The remaining amino group is elaborated to yield a terminal thiol acceptor. Condensation of the multiple hydrazides with an drug containing an aldehyde or ketone group yields a multiple acylhydrazone of the drug.

Conjugation of the linker to the targeting ligand is accomplished by the reaction of free thiol groups of the ligand, generated under controlled atmospheric conditions, with the terminal thiol acceptor of the linker.

Exemplary reaction schemes for preparation of the compounds of the invention are illustrated below. The compound numbers are cross referenced in the Example section hereof.

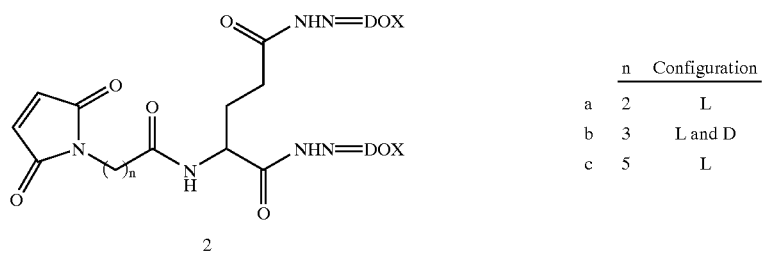

|   | n | Configuration |
|---|---|---|
| a | 2 | L |
| b | 3 | L and D |
| c | 5 | L |

2

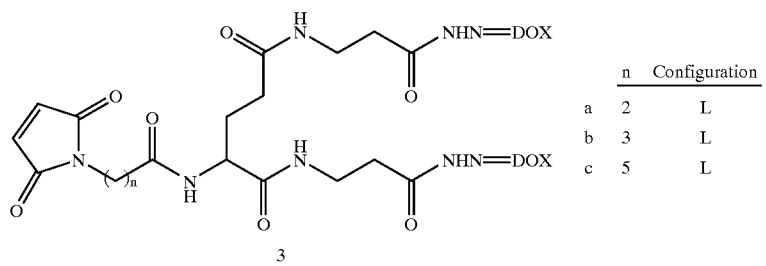

|   | n | Configuration |
|---|---|---|
| a | 2 | L |
| b | 3 | L |
| c | 5 | L |

3

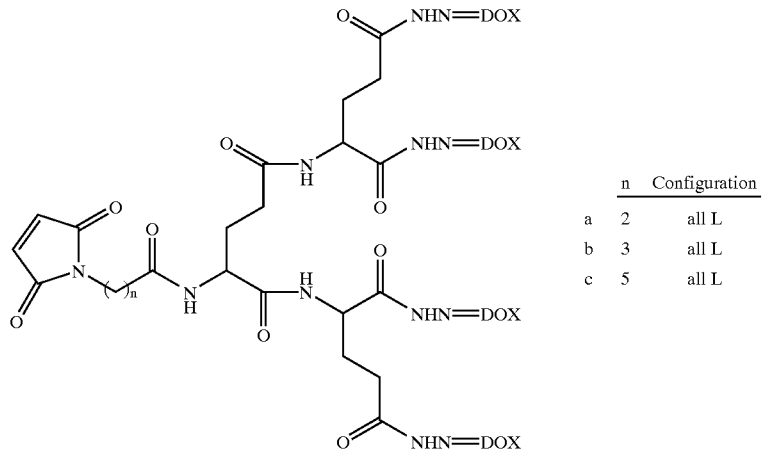

|   | n | Configuration |
|---|---|---|
| a | 2 | all L |
| b | 3 | all L |
| c | 5 | all L |

SCHEME 1
SYNTHESIS OF 2
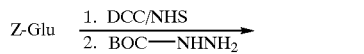
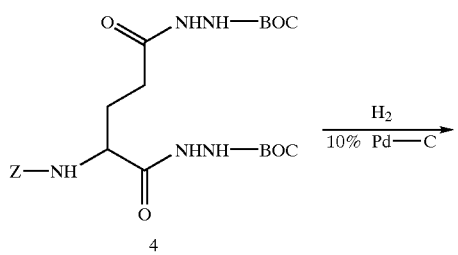
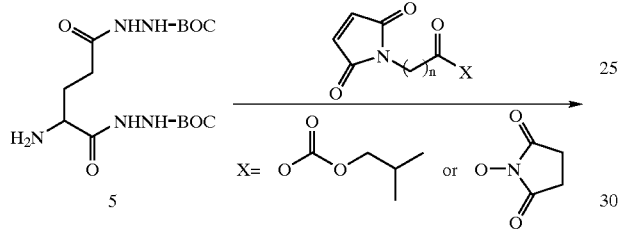
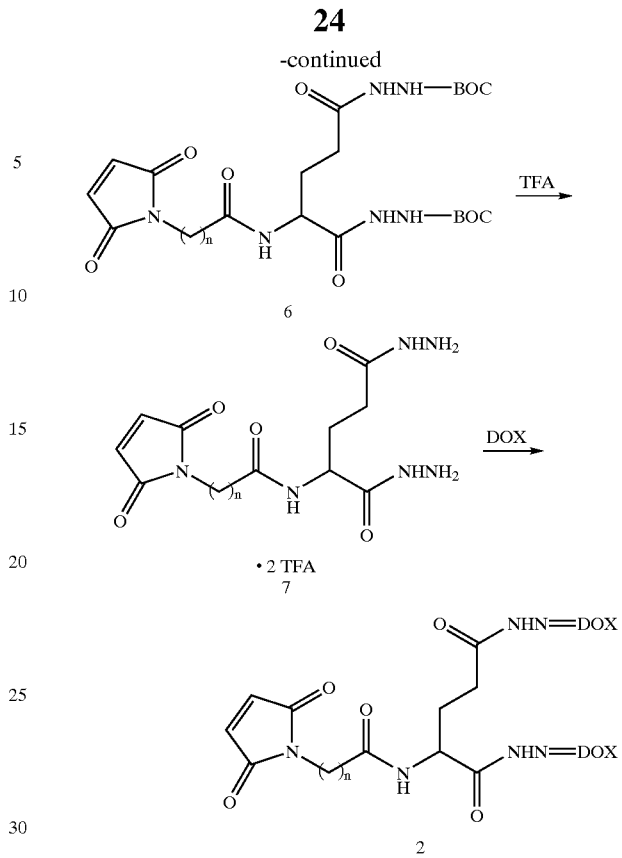
SCHEME II
SYNTHESIS OF 3
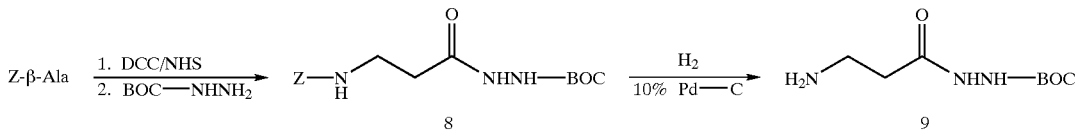
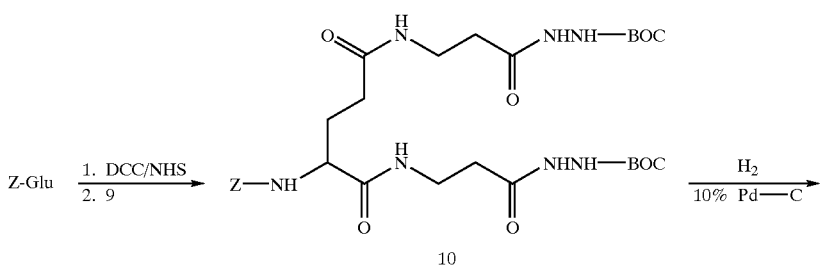
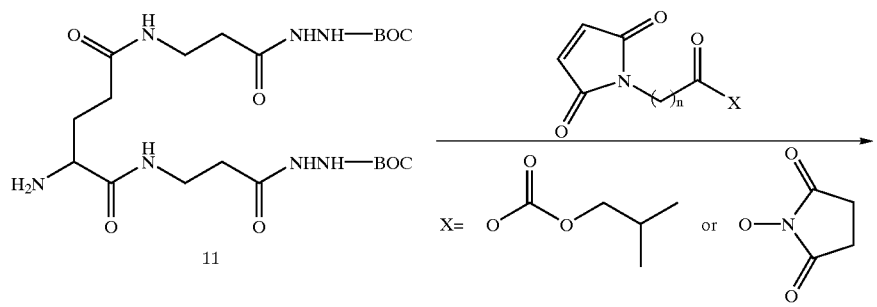

-continued
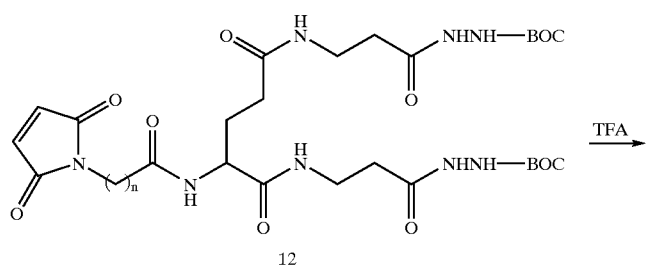
12
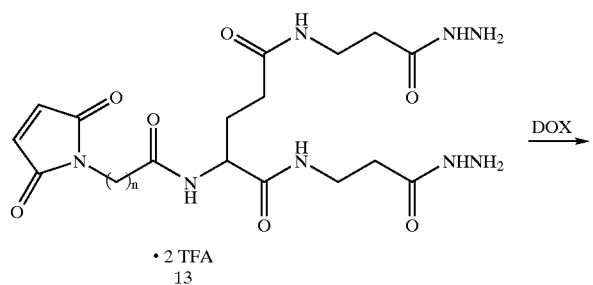
· 2 TFA
13
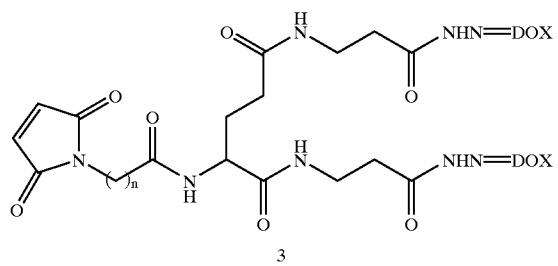
3
SCHEME III
SYNTHESIS OF 18
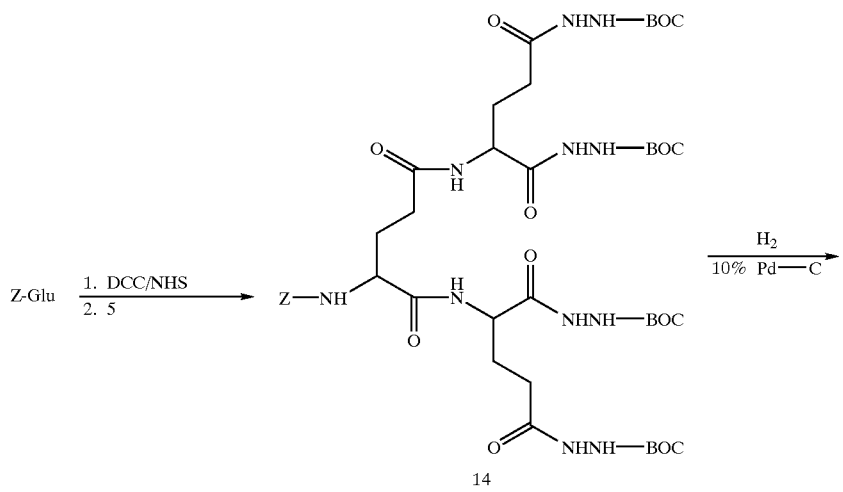
14

-continued
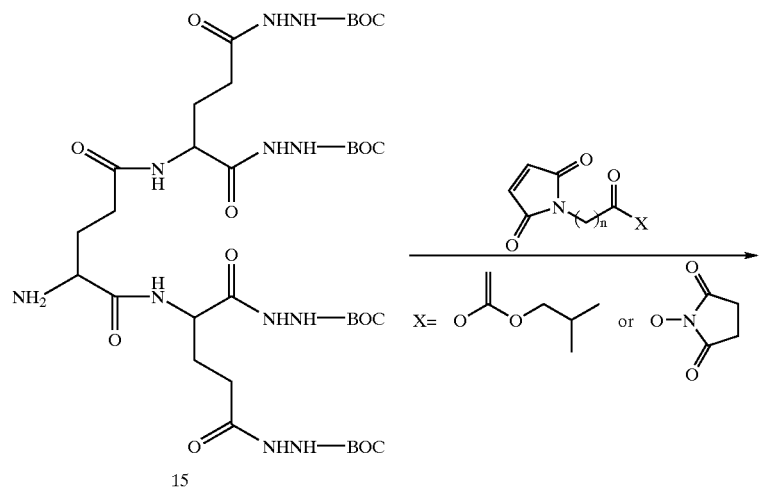
15
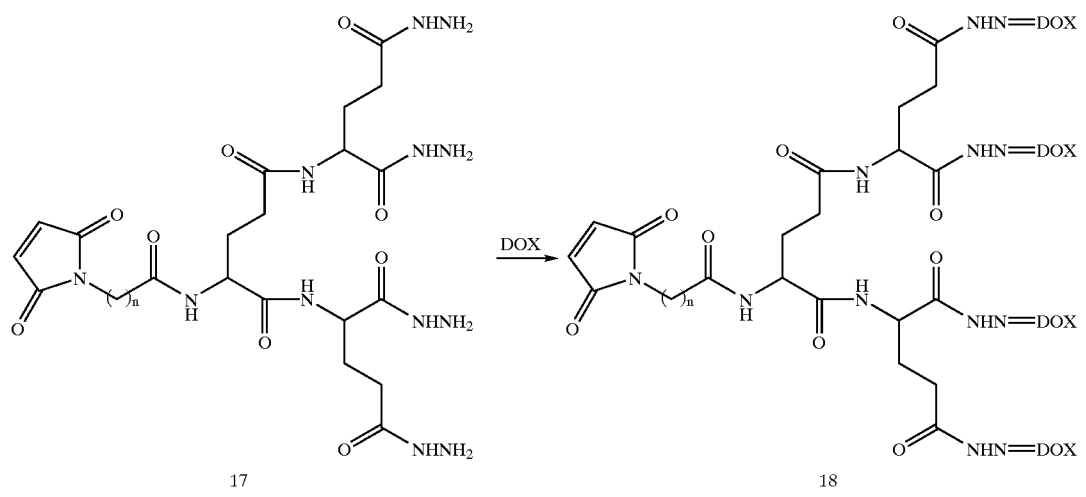

SCHEME IV
SYNTHESIS OF 26
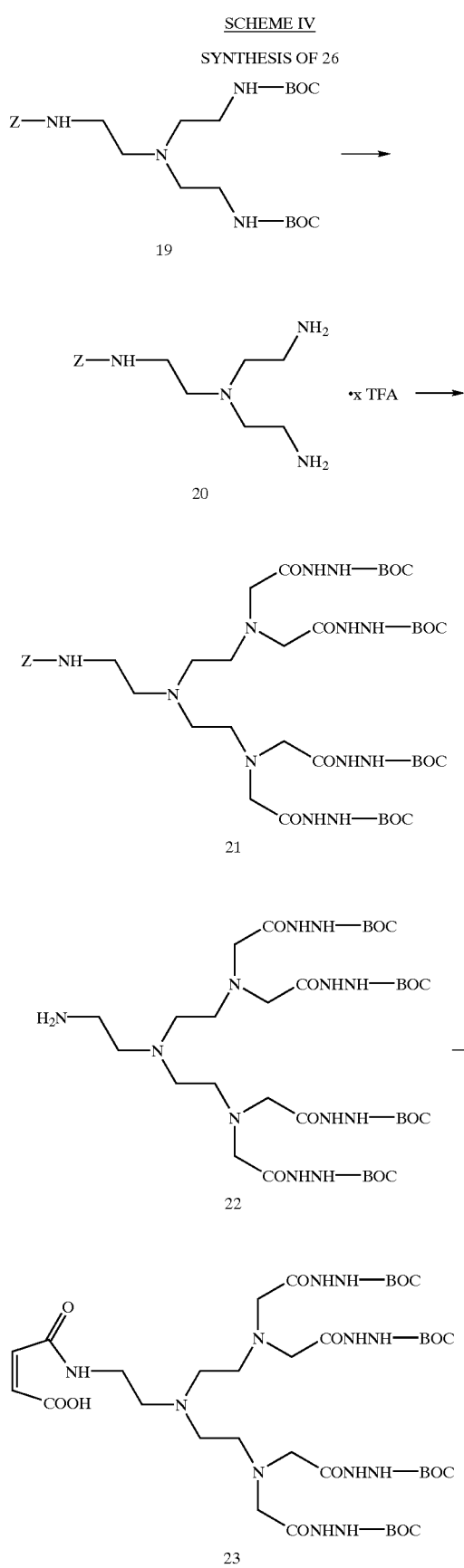
-continued
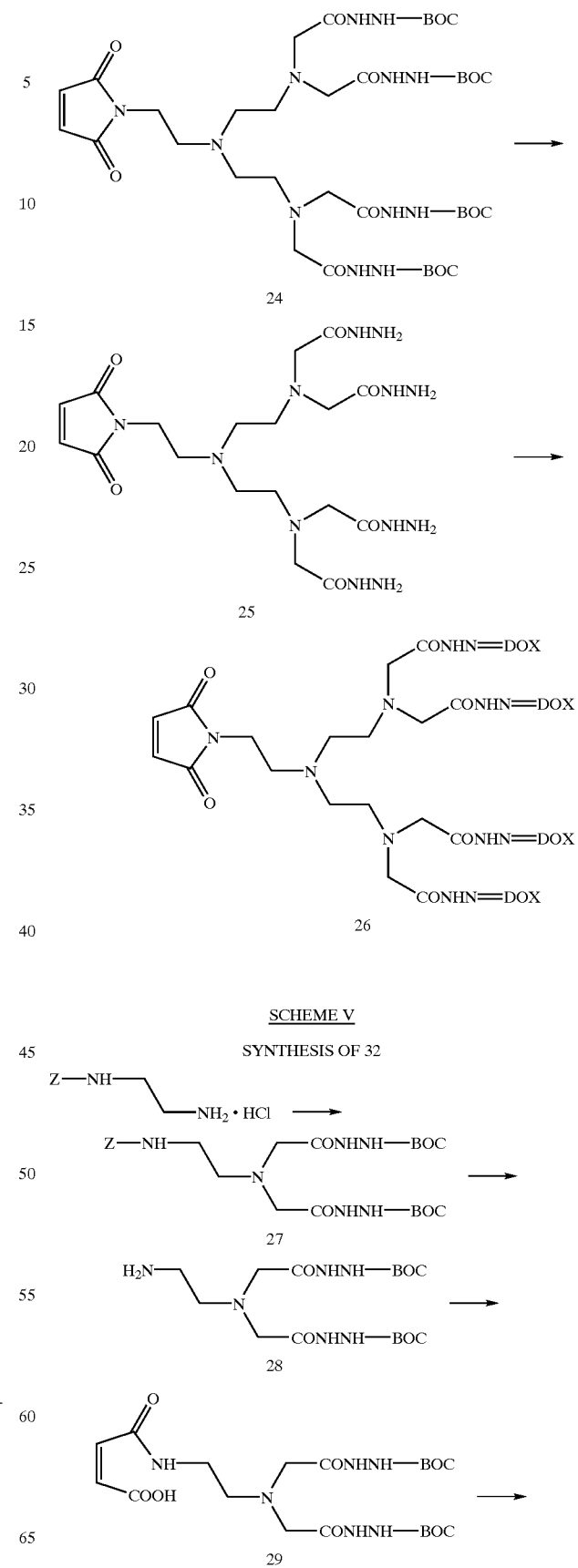
SCHEME V
SYNTHESIS OF 32

31
-continued
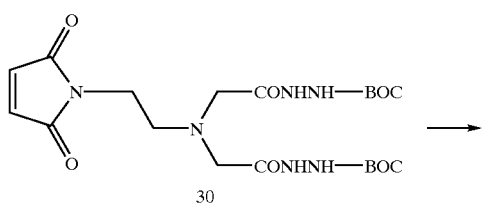
30
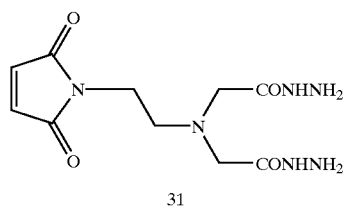
31
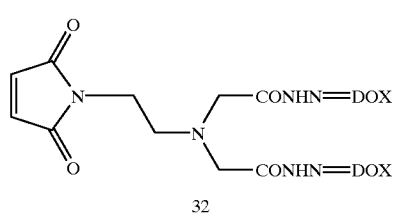
32
SCHEME VI
SYNTHESIS OF 38
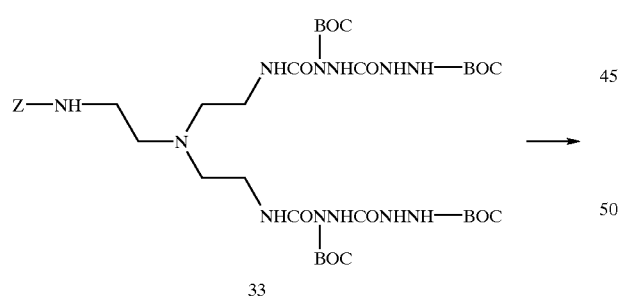
32
-continued
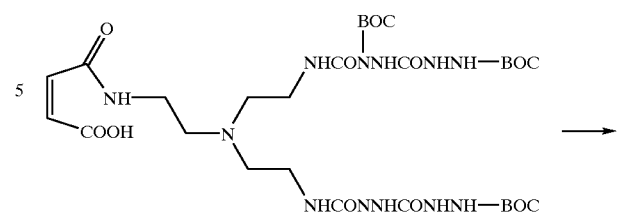
35
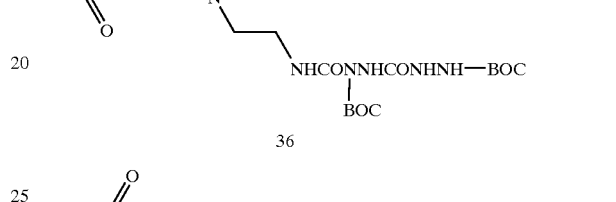
36
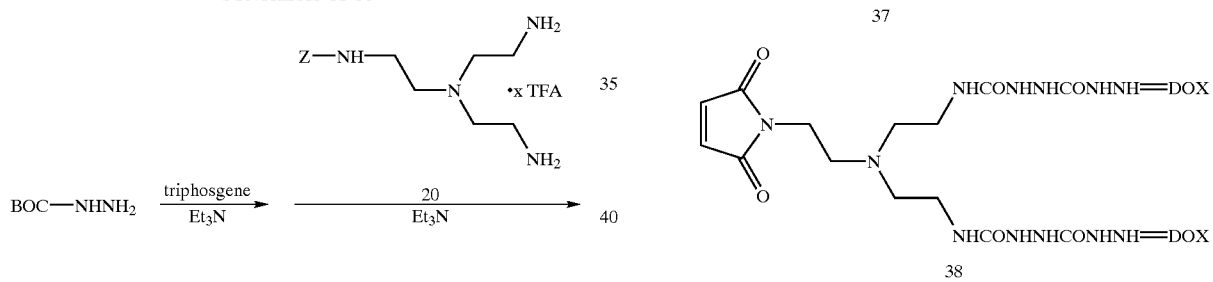
SCHEME VII
SYNTHESIS OF 46
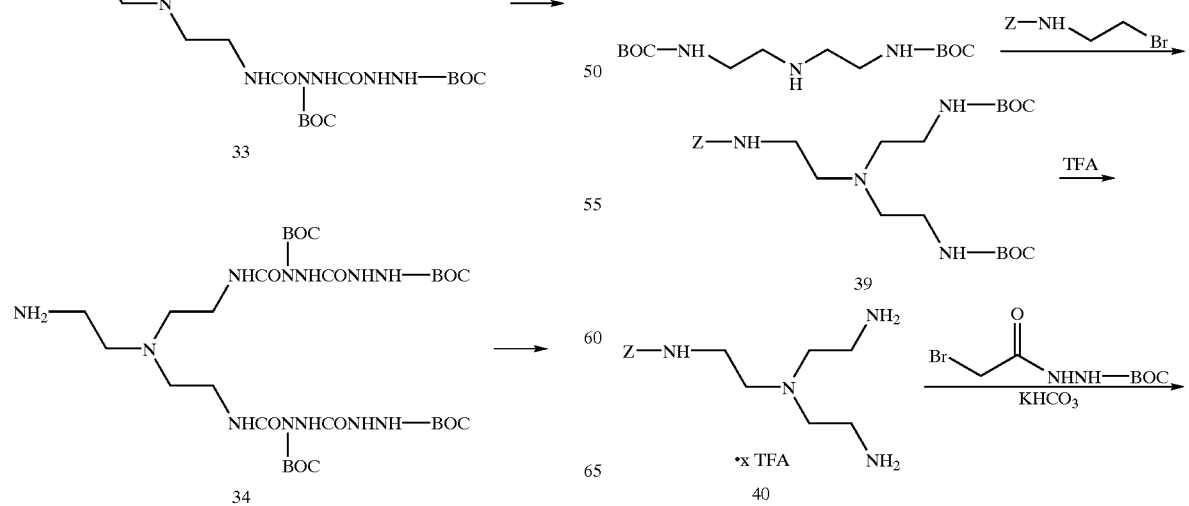

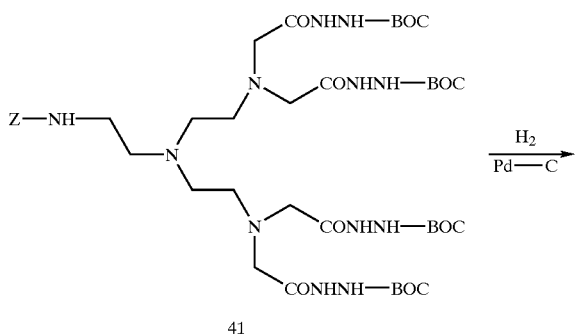
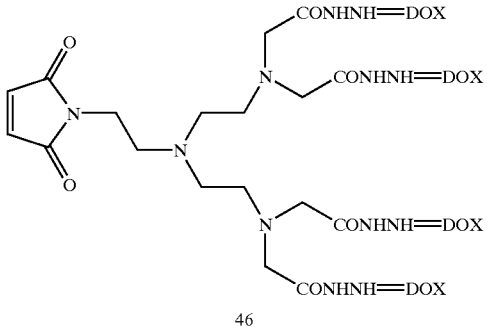

The abbreviations in the above reaction schemes have the following definitions: Z is carbobenzoxy, DCC is dicyclohexylcarbodiimide, BOC is t-butoxy carbonyl, TFA is trifluoroacetic acid, and DOX is doxorubicin.

The following examples are to illustrate the invention but should not be interpreted as a limitation thereon.

EXAMPLE 1

Z-Glutamyldi(Boc)hydrazide (Compound No. 4)

Z-Glutamic acid (42.20 g, 150 mmole) and N-hydroxy succinimide (34.53 g, 300 mmole) were dissolved in 150 ml DMF at 0° C. under dry $N_2$. A 0.5M solution of dicyclohexylcarbodiimide in methylene chloride (600 ml, 300 mmole) was added dropwise over a 1 hour period with stirring. The reaction was stored at 4° C. in the refrigerator for 18 hr. Dicyclohexylurea precipitate (65.48 g, 98%) was filtered, and the filtrate was added directly to solid t-butylcarbazate (39.65 g, 300 mmole). After stirring at room temperature for 48 hr., the reaction was rotary evaporated to an oil, which was redissolved in 300 ml ethyl acetate/200 ml ether. The organic layer was extracted three times with 200 ml 10% citric acid, 3 times with 200 ml saturated aqueous sodium bicarbonate, and once with 100 ml brine. The organic layer was dried over sodium sulfate and rotary evaporated to a foam. Flash chromatography was carried out on silica gel (4 in.×19 in.) with ethyl acetate-hexane 2:1, 12 L. Pure fractions containing product (4) were pooled and concentrated to a foam by rotary evaporation to yield, after drying under high vacuum, 55.24 g (72%).

$^1$H-NMR (CDCl$_3$): δ 1.44 and 1.47 (2s, 18H), 1.9–2.4 (bm, 4H), 4.32 (bm, 1H), 5.06 (dd, 2H), 5.55 (d, 1H), 6.5 (bd, 2H), 7.31 (bm, 5H), 9.6 (s, 1H), and 9.9 (s, 1H).

TLC: $R_f$ 0.64, $CH_2Cl_2$/MeOH (9:1).

Mass Spec.: FAB 510 (M+H$^+$) 532 (M+Na$^+$), 548.1 (M+K$^+$)

Elemental Analysis for $C_{23}H_{35}N_5O_8$: Theoretical C, 54.21; H, 6.92; N, 13.74. Found C, 53.96;H, 6.91; N, 13.41.

EXAMPLE 2

Z-(D)-Glutamyldi(Boc)hydrazide (Compound No. D-4)

Z-(D)-Glutamic acid (42.20 g, 150 mmole) and N-hydroxy succinimide (34.53 g, 300 mmole) were dissolved in 150 ml DMF at 0° C. under dry $N_2$. A 0.5M solution of dicyclohexylcarbodiimide in methylene chloride (600 ml, 300 mmole) was added dropwise over a 1 hour period with stirring. The reaction was stored at 4° C. in the refrigerator for 18 hr. Dicyclohexylurea precipitate (64.97 g, 97%) was filtered, and the filltrate was added directly to solid t-butylcarbazate (39.65 g, 300 mmole). After stirring at room temperature for 48 hr., the reaction was rotary evaporated to an oil, which was redissolved in 300 ml ethyl acetate/200 ml ether. The organic layer was extracted three times with 200 ml 10% citric acid, 3 times with 200 ml saturated aqueous sodium bicarbonate, and once with 100 ml brine. The organic layer was dried over sodium sulfate and rotary evaporated to a foam. Flash chromatography was carried out on silica gel (4 in.×18 in.) with the following gradient: (1) $CH_2Cl_2$, 2 L, (2) $CH_2Cl_2$-methanol 25:1, 4 L, and (3) $CH_2Cl_2$-methanol 9:1, 6 L. Pure fractions containing product (1), which eluted in $CH_2Cl_2$-methanol 9:1, were pooled and concentrated to a foam by rotary evaporation to yield, after drying under high vacuum, 59.11 g (77%).

$^1$H-NMR (CDCl$_3$): δ 1.44 and 1.47 (2s, 18H), 1.9–2.4 (bm, 4H), 4.32 (bm, 1H), 5.06 (dd, 2H), 5.57 (d, 1H), 6.6 (m, 2H), 7.31 (bm, 5H), 9.60 (s, 1H), and 9.87 (s, 1H).

TLC: $R_f$ 0.64, $CH_2Cl_2$/MeOH (9:1).

Mass Spec.: FAB 532 (M+Na$^+$), 549 (M+K$^+$)

Elemental Analysis for $C_{23}H_{35}N_5O_8$: Theoretical C, 54.21; H, 6.92; N, 13.74. Found C, 53.99;H, 6.92; N, 13.50.

EXAMPLE 3

Glutamyldi(Boc)hydrazide (Compound No. 5)

Z-Glutamyldi(Boc)hydrazide (4) (19.59 g, 38.44 mmole) was hydrogenated along with 2 g 10% Pd-C in 200 ml MeOH at 50 psi for 3 hr. The reaction was filtered through Celite and rotary evaporated. The resulting foam was dried under high vacuum to yield 5 (14.40 g, 100%).

$^1$H-NMR (d$_4$-Methanol): δ 1.42 and 1.45 (2s, 18H) , 1.9 (bm, 2H), 2.35 (t, 2H), 3.34 (t, 1H).

TLC: $R_f$ 0.34, $CH_2Cl_2$/MeOH (9:1).

Mass Spec.: DCI 376 (M+H)$^+$.

Elemental Analysis for $C_{15}H_{29}N_5O_6$·0.5 H$_2$O: Theoretical C, 46.87; H, 7.87; N, 18.22. Found C, 46.96; H, 7.74; N, 18.02.

EXAMPLE 4

(D)-Glutamyldi(Boc)hydrazide (Compound No. D-5)

Z-(D)-Glutamyldi(Boc)hydrazide (D-4) (23.05 g, 45.2 mmole) was hydrogenated along with 2 g 10% Pd-C in 200 ml MeOH at 50 psi for 4 hr. After filtration through Celite and rotary evaporation, a foam was obtained. Flash chromatography on silica gel (2 in.×20 in.) was carried out with the following gradient: (1) $CH_2Cl_2$-methanol 25:1, 600 ml, (2) $CH_2Cl_2$-methanol 9:1, 6 L, and (3) $CH_2Cl_2$-methanol 8:2, 4 L. Pure fractions were pooled and rotary evaporated. Drying under high vacuum yielded D-5 (13.51 g, 80%).

$^1$H-NMR (d$_4$-Methanol): δ 1.46 and 1.47 (2s, 18H), 1.94 (bm, 2H), 2.33 (t, 2H), 3.34 (t,1H).

TLC: $R_f$ 0.34, $CH_2Cl_2$/MeOH (9:1).

Mass Spec.: FAB 376 (M+H)$^+$, 398 (M+Na)$^+$, 414 (M+K)$^+$.

Elemental Analysis for $C_{15}H_{29}N_5O_6$·0.5 H$_2$O: Theoretical C, 46.87; H, 7.87; N, 18.22. Found C, 46.85; H, 7.63; N, 17.98.

EXAMPLE 5

Maleimidopropionylglutamyldi(Boc)hydrazide (Compound No. 6a)

Maleimidopropionic acid (636 mg, 3.76 mmole) and N-hydroxysuccinimide (476 mg, 4.14 mmole) were dissolved in 10 ml DMF at 0° C. A 0.5M solution of DCC in $CH_2Cl_2$ (7.6 ml, 3.8 mmole) was added, and the reaction allowed to stand for 20 hr. at 4° C. After filtration of the DCU precipitate, the filtrate was added to 5 (1.27 g, 3.38 mmole) and stirred at room temperature for 2.5 days. Solvents were partially removed by rotary evaporation. The oil was dissolved in 100 ml ethyl acetate, then extracted three times with 100 ml 10% citric acid, three times with 100 ml saturated aqueous sodium bicarbonate, and three times with 100 ml H$_2$O. The organic layer was dried over sodium sulfate and rotary evaporated to a foam. This was purified by flash chromatography on silica gel (2 in.×11 in.) with $CH_2Cl_2$-acetic acid-methanol 93:2:5. Pure fractions were pooled, rotary evaporated, and dried under high vacuum to yield 6a as a foam (1.22 g, 69%).

$^1$H-NMR (d$_4$-Methanol): δ 1.46 (s, 18H), 2.01 (m), 2H), 2.33 (t, 2H), 2.51 (t, 2H), 3.76 (t, 2H), 4.34 (t, 1H), 6.80 (s, 2H).

TLC: $R_f$ 0.54, $CH_2Cl_2$-acetic acid-methanol 90:2:8.

Mass Spec.: FAB 549.4 (M+Na)$^+$, 565.3 (M+K)$^+$

Elemental Analysis for $C_{22}H_{34}N_6O_9$·2HOAc: Theoretical C, 48.29; H, 6.55; N, 13.00. Found C, 48.15; H, 6.48; N, 13.28.

EXAMPLE 6

Maleimidobutyrylglutamyldi(Boc)hydrazide (Compound No. 6b)

Maleimidobutyric acid (1.9 g, 10.3 mmole) and N-hydroxy succinimide (2.7 g, 23.5 mmole) were dissolved in 25 ml DMF at 0° C. A 0.5M solution of DCC in $CH_2Cl_2$ (45 ml, 22.5 mmole) was added, and the reaction allowed to stand for 16 hr. at 4° C. After filtration of the DCU precipitate, the filtrate was added to 5 (7.7 g, 20.5 mmole) and the reaction stored at 4° C. for four days. Solvents were removed by rotary evaporation. The oil was dissolved in 100 ml ethyl acetate, then extracted three times with 100 ml 10% citric acid, three times with 100 ml saturated aqueous sodium bicarbonate, and three times with 100 ml H$_2$O. The organic layer was dried over sodium sulfate and rotary evaporated to a foam. This was purified through a plug of silica gel with $CH_2Cl_2$-acetic acid-methanol 93:2:5, rotary evaporated, and dried under high vacuum to yield 6b as a foam (3.50 g, 63%).

$^1$H-NMR (d$_4$-Methanol): δ 1.36 and 1.37 (2s, 18H), 1.77 (p, 2H), 2.00 (bm, 2H), 2.14 (t, 2H), 2.26 (t, 2H), 3.43 (t, 2H), 4.26 (t, 1H), 6.71 (s, 2H).

TLC: $R_f$ 0.58, $CH_2Cl_2$-acetic acid-methanol 90:2:8.

Mass Spec.: 541 (M+H)$^+$, 563 (M+Na)$^+$, 579 (M+K)$^+$

Elemental Analysis for $C_{23}H_{36}N_6O_9$·0.75 H$_2$O: Theoretical C, 49.86; H, 6.82; N, 15.17. Found C, 50.21; H, 6.72; N, 14.79.

EXAMPLE 7

Maleimidobutyryl-(D)-glutamyldi(Boc)hydrazide (Compound No. D-6b)

Maleimidobutyric acid (1.832 g, 10.0 mmole) was dissolved with N-Methylmorpholine (1.21 ml, 11.0 mmole) in 60 ml dry THF under N$_2$ at 0° C. Isobutylchloroformate (1.30 ml, 10.0 mmole) was added dropwise, followed 10 minutes later by the addition of (D)-Glutamyldi(Boc) hydrazide (D-5) (3.754 g, 10.0 mmole). Stirring was continued for 1 hour at 0° C. The reaction was rotary evaporated to a foam, which was then dissolved in 150 ml EtOAc. The organic layer was washed two times with 100 ml 10% citric acid and two times with 100 ml saturated NaHCO$_3$. The organic layer was concentrated to a foam, which was purified by flash chromatography on silica gel (2 in.×11 in.) with CH$_2$Cl$_2$-acetic acid-methanol 95:2:3, 2 L followed by CH$_2$Cl$_2$-acetic acid-methanol 93:2:5, 1 L. Pure fractions were pooled and rotary evaporated to a foam. Drying under high vacuum yielded 3 (3.25 g, 60%).

$^1$H-NMR (d$_4$-Methanol): δ 1.45 and 1.46 (2s, 18H), 1.86 (m, 2H), 2.09 (bm, 2H), 2.24 (t, 2H), 2.35 (t, 2H), 3.52 (t, 2H), 4.35 (t, 1H), 6.81 (s, 2H).

TLC: R$_f$ 0.51, CH$_2$Cl$_2$-acetic acid-methanol 90:5:5.

Mass Spec.: 563 (M+Na)$^+$, 579 (M+K)$^+$

Elemental Analysis for C$_{23}$H$_{36}$N$_6$O$_9$.0.75 H2O: Theoretical C, 49.86; H, 6.82; N, 15.17. Found C, 50.25; H, 6.65; N, 14.80.

EXAMPLE 8

Maleimidocaproylglutamyldi(Boc)hydrazide (Compound No. 6c)

Maleimidocaproic acid (4.22 g, 20 mmole) and N-hydroxysuccinimide (2.53 g, 22 mmole) were dissolved in 25 ml DMF at 0° C. A 0.5M solution of DCC in CH$_2$Cl$_2$ (40 ml, 20 mmole) was added, and the reaction allowed to stand for 20 hr. at 4° C. After filtration of the DCU precipitate, the filtrate was added to 5 (7.88 g, 21 mmole) and the reaction stirred at room temperature for 6 hr. Solvents were removed by rotary evaporation. The oil was dissolved in 100 ml ethyl acetate, then extracted three times with 100 ml 10% citric acid, three times with 100 ml saturated aqueous sodium bicarbonate, and three times with 100 ml H$_2$O. The organic layer was dried over sodium sulfate and rotary evaporated to a foam. This was purified by flash chromatography on silica gel (2 in.×10 in.) with 4 L CH$_2$Cl$_2$-acetic acid-methanol 97:1:2. Pure fractions were pooled, rotary evaporated, and dried under high vacuum to yield 6c as a foam (6.40 g, 56%).

$^1$H-NMR (d$_4$-Methanol): δ 1.2 (p, 2H), 1.40 (s, 18H), 1.5 (m, 4H), 2.0 (bm, 2H), 2.14 (t, 2H), 2.28 (t, 2H), 3.41 (t, 2H), 4.29 (t, 1H), 6.72 (s, 2H).

TLC: R$_f$ 0.30, CH$_2$Cl$_2$-acetic acid-methanol 93:2:5.

Mass Spec.: FAB 569 (M+H)$^+$, 591 (M+Na)$^+$, 607 (M+K)$^+$

Elemental Analysis for C$_{25}$H$_{40}$N$_6$O$_9$.0.5 H$_2$O: Theoretical C, 51.98; H, 7.15; N, 14.55. Found C, 51.79; H, 6.96; N, 14.39.

EXAMPLE 9

Maleimidopropionylglutamyldihydrazide ditrifluoroacetate (Compound No. 7a)

Maleimidopropionylglutamyldi(Boc)hydrazide (6a) (1.50 g, 2.85 mmole) was stirred in 15 ml CH$_2$Cl$_2$/trifluoroacetic acid (1:1) under N$_2$ for 1.5 hr. Solvents were removed by rotary evaporation. Ether was added and co-evaporated three times, then the resulting solid was triturated with ether. The solid was filtered and dried under high vacuum to yield 7a (1.6 g, 100%)

$^1$H-NMR (d$_4$-Methanol): δ 1.99 and 2.16 (2m, 2H), 2.41 (t, 2H), 2.53 (t, 2H), 3.80 (t, 2H), 4.38 (dd, 1H), 6.81 (s, 2H).

Mass Spec.: FAB 349.2 (M+Na)$^+$, 365.1 (M+K)$^+$

Elemental Analysis for C$_{12}$H$_{18}$N$_6$O$_5$.2.8 TFA: δTheoretical C, 32.75; H, 3.25; N, 13.02. Found C, 33.04; H, 3.37; N, 12.72.

EXAMPLE 10

Maleimidobutyrylglutamyldihydrazide ditrifluoroacetate (Compound No. 7b)

Maleimidobutyrylglutamyldi(Boc)hydrazide (6b) (3.50 g, 6.47 mmole) was stirred in 40 ml CH$_2$Cl$_2$/trifluoroacetic acid (1:1) under N$_2$ for 2 hr. Solvents were removed by rotary evaporation. Ether was added and co-evaporated three times, then the resulting solid was triturated with ether. The solid was filtered and dried under high vacuum to yield 7b (3.8 g, 100%)

$^1$H-NMR (d$_4$-Methanol): δ 1.87 (p, 2H), 2.0 and 2.2 (2m, 2H), 2.27 (t, 2H), 2.44 (m, 2H), 3.53 (t, 2H), 4.42 (dd, 1H), 6.82 (s, 2H).

Mass Spec.: FAB 341 (M+H)$^+$, 363 (M+Na)$^+$, 379 (M+K)$^+$

Elemental Analysis for C$_{13}$H$_{20}$N$_6$O$_5$.3.15 TFA: Theoretical C, 33.14; H, 3.34; N, 12.01. Found C, 33.49; H, 3.52; N, 11.64.

EXAMPLE 11

Maleimidobutyryl-(D)-glutamyldihydrazide ditrifluoroacetate (Compound No. D-7b)

Maleimidobutyryl-(D)-glutamyldi(Boc)hydrazide (D-6b) (2.06 g, 3.81 mmole) was stirred in 40 ml CH$_2$Cl$_2$ with 40 ml trifluoroacetic acid under N$_2$ for 1 hr. Solvents were removed by rotary evaporation. Ether was added and co-evaporated three times, then the resulting solid was triturated with ether. The solid was filtered and dried under high vacuum to yield D-7b (2.2 g, 100%)

$^1$H-NMR (d$_4$-Methanol): δ 1.79 (p, 2H), 1.9 and 2.1 (2m, 2H), 2.18 (t, 2H), 2.37 (m, 2H), 3.45 (t, 2H), 4.35 (dd, 1H), 6.73 (s, 2H).

EXAMPLE 12

Maleimidocaproylglutamyldihydrazide ditrifluoroacetate (Compound No. 7c)

Maleimidocaproylglutamyldi(Boc)hydrazide (6c) (5.96 g, 10.5 mmole) was stirred in 100 ml CH$_2$Cl$_2$/trifluoroacetic acid (1:1) under N$_2$ for 1 hr. Solvents were removed by rotary evaporation. Ether was added and co-evaporated three times, then the resulting solid was triturated with ether. The solid was filtered and dried under high vacuum to yield 7c (6.3 g, 100%)

$^1$H-NMR (d$_4$-Methanol): δ 1.22 (p, 2H), 1.52 (s, 4H), 1.92 and 2.09 (2m, 2H), 2.18 (t, 2H), 2.35 (m, 2H), 3.41 (t, 2H), 4.35 (dd, 1H), 6.72 (s, 2H).

Mass Spec.: FAB 369 (M+H)$^+$, 391 (M+Na)$^+$, 407 (M+K)$^+$

Elemental Analysis for C$_{15}$H$_{24}$N$_6$O$_5$.2.5TFA: Theoretical C, 36.76; H, 4.09; N, 12.86. Found C, 36.66; H, 4.22; N, 12.72.

EXAMPLE 13

Maleimidopropionylglutamyldihydrazone of Doxorubicin (Compound No. 2a "MP-Glu(DOX)$_2$")

Maleimidopropionylglutamyldihydrazide ditrifluoroacetate (7a) (600 mg, 1.07 mmole) and DOX.HCl (1.24 g, 2.14 mmole) were dissolved in 600 ml methanol over a period of 3 hours. The reaction was concentrated to 100 ml by rotary evaporation, then stirred for 3 days. The reaction was further concentrated to 12 ml and eluted on an LH-20 column (2"×10") with methanol.

Chromatography was repeated in the same system on mixed fractions. The purified product was rotary evaporated to a red film and dried under high vacuum to yield 2a (776 mg, 50%).

$^1$H-NMR (d$_4$-Methanol): (selected peaks) δ 1.34 (2d, 6H), 4.07 (2s, 6H), 6.79 (s, 2H), 7.5–8.0 (m, 6H).

Mass Spec.: FAB 1375.4 (M–H)$^+$; Ionspray 1377.2 MH$^+$.

Elemental Analysis for $C_{66}H_{72}N_8O_{25}$·2HCl·3.0H$_2$O: Theoretical C, 52.70; H, 5.36; N, 7.45. Found C, 52.57; H, 5.25; N, 7.33.

EXAMPLE 14

Maleimidobutyrylglutamyldihydrazone of Doxorubicin (Compound No. 2b "MBGlu(DOX)$_2$")

Maleimidobutyrylglutamyldihydrazide ditrifluoroacetate (7b) (1.00 g, 1.76 mmole) and DOX.HCl (2.05 g, 3.53 mmole) were dissolved in 800 ml methanol over a period of 3 hours. The reaction was concentrated to 150 ml by rotary evaporation, then stirred for 1.5 days. The reaction was further concentrated to 20 ml and eluted on an LH-20 column (2"×12") with methanol.

Chromatography was repeated in the same system on mixed fractions. The purified product was rotary evaporated to a red film and dried under high vacuum to yield 2b (1.32 g, 51%).

$^1$H-NMR (d$_4$-Methanol): (selected peaks) δ 1.33 (2d, 6H), 4.06 (2s, 6H), 6.80 (s, 2H), 7.5–8.0 (m, 6H).

Mass Spec.: FAB 1392 MH$^+$, 1413.4 (M+Na)$^+$, 1429 (M+K)$^+$.

Ionspray 1392.5 (M+H)$^+$, 1414.4 (M+Na)$^+$

Elemental Analysis for $C_{67}H_{74}N_8O_{25}$·2HCl·4.0H$_2$O: Theoretical C, 52.38; H, 5.51; N, 7.29. Found C, 52.38; H, 5.58; N, 7.50.

EXAMPLE 15

Maleimidobutyryl-(D)-glutamyldihydrazone of Doxorubicin (Compound No. D-2b "MB-D-Glu(DOX)$_2$")

Maleimidobutyryl-(D)-glutamyldihydrazide ditrifluoroacetate (D-7b) (570 mg, 1.00 mmole) and DOX.HCl (1.34 g, 2.30 mmole) were dissolved in 600 ml methanol over a period of 3 hours. The reaction was concentrated to 100 ml by rotary evaporation, then stirred for 2.5 days. The reaction was further concentrated to 50 ml and eluted on an LH-20 column (2"×10") with methanol. Chromatography was repeated in the same system on mixed fractions. The purified product was rotary evaporated to a red film and dried under high vacuum to yield D-2b (420 mg, 30%).

$^1$H-NMR (d$_4$-Methanol): (selected peaks) δ 1.30 (2d, 6H), 4.07 (2s, 6H), 6.80 (s, 2H), 7.5–8.0 (m, 6H).

Mass Spec.: FAB 1392.0 MH$^+$, 1414.9 (M+Na)$^+$, 1429.7 (M+K)$^+$.

Elemental Analysis for $C_{67}H_{74}N_8O_{25}$·2HCl·3.5H$_2$O: Theoretical C, 52.69; H, 5.48; N, 7.34; Cl, 4.64. Found C, 52.74; H, 5.57; N, 7.47; Cl, 5.28.

EXAMPLE 16

Maleimidocaproylglutamyldihydrazone of Doxorubicin (Compound No. 2c "MCGlu(DOX)2")

Maleimidocaproylglutamyldihydrazide ditrifluoroacetate (7c) (298 mg, 0.50 mmole) and DOX.HCl (580 mg, 1.00 mmole) were dissolved in 350 ml methanol over a period of 3 hours. The reaction was concentrated to 50 ml by rotary evaporation, then stirred for 3 days. The reaction was further concentrated to 5 ml and eluted on an LH-20 column (2"×10") with methanol. The purified product was rotary evaporated to a red film and dried under high vacuum to yield 2c (510 mg, 68%).

$^1$H-NMR (d$_4$-Methanol): (selected peaks) δ 1.34 (2d, 6H), 4.08 (2s, 6H), 6.76 (s, 2H), 7.5–8.0 (m, 6H).

Mass Spec.: FAB 1420 MH$^+$, 1442.3 (M+Na)$^+$. Ionspray 1419.6 (M+H)$^+$.

HRMS: calculated 1419.5156; observed 1419.5191.

Elemental Analysis for $C_{69}H_{78}N_8O_{25}$·2HCl·4H$_2$O: Theoretical C, 52.98; H, 5.67; N, 7.16. Found C, 52.96; H, 5.39; N, 7.45.

EXAMPLE 17

Z-β-Alanyl(BOC)hydrazide (Compound No. 8)

Z-β-Alanine (8.93 g, 40 mmole), t-butylcarbazate (5.29 g, 40 mmole), and EDCI (8.00 g, 42 mmole) were stirred in 200 ml CH$_2$Cl$_2$ for 1.5 hr. at room temperature. The reaction was extracted three times with 200 ml 0.1 M acetic acid, twice with 200 ml saturated aqueous sodium bicarbonate, and once with 200 ml water. The organic layer was dried over sodium sulfate, rotary evaporated, and dried under high vacuum to yield 8 as a foam, 12.42 g (92%).

$^1$H-NMR (d$_6$-DMSO): δ 1.38 (s, 9H), 2.25 (t, 2H), 3.19 (q, 2H), 4.99 (s, 2H), 7.3 (m, 6H), 8.21 (s, 1H), 9.56 (s, 1H).

TLC: R$_f$ 0.58, CH$_2$Cl$_2$/MeOH (9:1).

Mass Spec.: FAB 338 (M+H)$^+$.

Elemental Analysis for $C_{16}H_{23}N_3O_5$: Theoretical C, 56.96; H, 6.87; N, 12.45. Found C, 57.19; H, 7.05; N, 12.57.

EXAMPLE 18

β-Alanyl(BOC)hydrazide (Compound No. 9)

8 (15.25 g, 45.2 mmole) was hydrogenated at 50 psi in 200 ml methanol with 3 g 10% Pd-C for 4 hours. The reaction was filtered through Celite, rotary evaporated, and dried under high vacuum to yield 9 as a hygroscopic foam, 9.2 g (100%).

$^1$H-NMR (d$_4$-Methanol): δ 1.40 (s, 9H), 2.32 (t, 2H), 2.88 (t, 2H).

Mass Spec.: FAB 204.2 (M+H)$^+$.

Elemental Analysis for $C_8H_{17}N_3O_3$·0.5H$_2$O: Theoretical C, 45.27; H, 8.55; N, 19.80. Found C, 45.51; H, 8.17; N, 19.49.

EXAMPLE 19

Z-Glutamyldi[β-Alanyl(Boc)hydrazide] (Compound No. 10)

Z-Glutamic acid (3.86 g, 13.7 mmole) and N-hydroxy succinimide (3.17 g, 27.5 mmole) were dissolved in 80 ml DMF at 0° C. under dry N$_2$. A 0.5M solution of dicyclohexylcarbodiimide in methylene chloride (55 ml, 27.5 mmole) was added and the reaction was stored at 4° C. for 24 hr. Dicyclohexylurea precipitate was filtered, and the filltrate was added to 9 (6.00 g, 29.5 mmole). After stirring at room temperature for 15 hr., the reaction was rotary evaporated to an oil, which was redissolved in 150 ml ethyl acetate. The organic layer was extracted three times with 100 ml 10% citric acid, 3 times with 100 ml saturated aqueous sodium bicarbonate, and three times with 100 ml brine. The organic layer was dried over sodium sulfate and rotary evaporated to a foam. Flash chromatography was carried out on silica gel (2 in.×11 in.) with 1 L $CH_2Cl_2$/methanol 25:1 followed by 3 L $CH_2Cl_2$/methanol 9:1. Pure fractions containing product (10) were pooled and concentrated to a foam by rotary evaporation to yield, after drying under high vacuum, 6.70 g (75%).

$^1$H-NMR ($CDCl_3$): δ 1.42 (s, 18H), 2.03 and 2.32 (2m, 8H), 3.5 (m, 4H), 4.35 (t, 1H), 5.05 (dd, 2H), 6.22 (d, 1H), 6.49 (d, 2H), 7.30 (s, 5H), 7.42 (m, 1H), 7.58 (m, 1H).

TLC: Rf 0.40, $CH_2Cl_2$/MeOH 9:1.

Mass Spec.: DCI 652 (M+H)$^+$, 674 (M+Na)$^+$, 690 (M+K)$^+$.

Elemental Analysis for $C_{29}H_{45}N_7O_{10}$: Theoretical C, 53.45; H, 6.96; N, 15.04. Found C, 53.10; H, 6.90; N, 14.91.

EXAMPLE 20

Glutamyldi[β-Alanyl(Boc)hydrazide] (Compound No. 11)

Z-Glutamyldi[β-Alanyl(Boc)hydrazide] (10) (3.52 g, 5.40 mmole) was hydrogenated along with 1 g 10% Pd-C in 75 ml MeOH at 50 psi for 2 hr. The reaction was filtered through Celite and rotary evaporated. The resulting foam was dried under high vacuum to yield 11 (2.77 g, 99%).

$^1$H-NMR ($d_4$-Methanol): δ 1.46 (s, 18H), 1.91 (m, 2H), 2.25 (t, 2H), 2.42 (q, 4H), 3.35 (t, 1H), 3.44 (m, 4H).

Mass Spec.: FAB 518 (M+H)$^+$, 540 (M+Na)$^+$, 556 (M+K)$^+$.

Elemental Analysis for $C_{21}H_{39}N_7O_8 \cdot 1.5H_2O$: Theoretical C, 46.31; H, 7.77; N, 18.00. Found C, 46.34; H, 7.42; N, 17.90.

EXAMPLE 21

Maleimidopropionylglutamyldi[β-Alanyl(Boc) hydrazide] (Compound No. 12a)

Maleimidopropionic acid (0.399 mg, 2.36 mmole) and N-hydroxy succinimide (272 mg, 2.36 mmole) were dissolved in 30 ml $CH_2Cl_2$/3 ml DMF at 0° C. A 0.5M solution of DCC in $CH_2Cl_2$ (4.7 ml, 2.36 mmole) was added, and the reaction stirred for 3 hr. at room temperature. After filtration of the DCU precipitate, the filtrate was added to 11 (1.10 g, 2.13 mmole) and the reaction stirred at room temperature for one day. Solvents were removed by rotary evaporation. The oil was purified by flash chromatography on silica gel (2 in.×10 in.) with 500 ml $CH_2Cl_2$, 2 L $CH_2Cl_2$/methanol 95:5, and 2 L $CH_2Cl_2$/methanol 9:1. Pure fractions were pooled, rotary evaporated, and dried under high vacuum to yield 12a as a foam (850 mg, 60%).

$^1$H-NMR ($d_4$-Methanol): δ 1.46 (s, 18H), 1.82 and 2.04 (2m, 2H), 2.23 (t, 2H), 2.40 (m, 4H), 2.52 (t, 2H), 3.45 (m, 4H), 3.78 (t, 2H), 4.20 (dd, 1H), 6.81 (s, 2H).

TLC: Rf 0.22, $CH_2Cl_2$/MeOH 9:1.

Mass Spec.: FAB 669 (M+H)$^+$, 691 (M+Na)$^+$, 707 (M+K)$^+$.

Elemental Analysis for $C_{28}H_{44}N_8O_{11} \cdot 2H_2O$: Theoretical C, 47.72; H, 6.87; N, 15.90. Found C, 47.70; H, 6.57; N, 15.83.

EXAMPLE 22

Maleimidobutyrylglutamyldi[β-Alanyl(Boc) hydrazide] (Compound No. 12b)

Maleimidobutyric acid (432 mg, 2.36 mmole) and N-hydroxy succinimide (272 mg, 2.36 mmole) were dissolved in 30 ml $CH_2Cl_2$/3 ml DMF at 0° C. A 0.5M solution of DCC in $CH_2Cl_2$ (4.7 ml, 2.36 mmole) was added, and the reaction stirred for 3 hr. at room temperature. After filtration of the DCU precipitate, the filtrate was added to 11 (1.10 g, 2.13 mmole) and the reaction stirred at room temperature for one day. Solvents were removed by rotary evaporation. The oil was purified by flash chromatography on silica gel (2 in.×10 in.) with 500 ml $CH_2Cl_2$, 2 L $CH_2Cl_2$/methanol 95:5, and 2 L $CH_2Cl_2$/methanol 9:1. Pure fractions were pooled, rotary evaporated, and dried under high vacuum to yield 12b as a foam (800 mg, 55%).

$^1$H-NMR ($d_4$-Methanol): δ 1.46 (s, 18H), 1.87 (m, 3H), 2.08 (m, 1H), 2.24 (m, 4H), 2.41 (m, 4H), 3.45 (m, 6H), 4.23 (dd, 1H), 6.82 (s, 2H).

TLC: Rf 0.20, $CH_2Cl_2$/MeOH 9:1.

Mass Spec.: FAB 683 (M+H)$^+$, 705 (M+Na)$^+$, 721 (M+K)$^+$.

Elemental Analysis for $C_{29}H_{46}N_8O_{11} \cdot 1.5H_2O$: Theoretical C, 49.08; H, 6.96; N, 15.79. Found C, 48.85; H, 6.65; N, 15.73.

EXAMPLE 23

Maleimidocaproylglutamyldi[β-Alanyl(Boc) hydrazide] (Compound No.12c)

Maleimidocaproic acid (453 mg, 2.14 mmole) and N-methylmorpholine (239 mg, 2.36 mmole) were dissolved in 25 ml dry THF under Ar at −5° C. Isobutylchloroformate (263 mg, 1.93 mmole) was added. After 5 min., 11 (1.0 g, 1.93 mmole) was added as a THF solution, and the reaction stirred for 3 hr. with warming to room temperature. Ethyl acetate (150 ml) was added, and then the solution was extracted three times with 75 ml 10% citric acid, three times with 75 ml saturated aqueous sodium bicarbonate, and three times with 75 ml water. The organic layer was dried over sodium sulfate, then passed through a plug of silica gel with $CH_2Cl_2$/methanol 9:1. The purified product was rotary evaporated, and dried under high vacuum to give 12c, 800 mg (58%).

$^1$H-NMR ($d_4$-Methanol): δ 1.30 (m, 2H), 1.46 (s, 18H), 1.60 (m, 4H), 1.88 and 2.06 (2m, 2H), 2.22 (t, 4H), 2.41 (t, 4H), 3.44 (m, 6H), 4.24 (dd, 1H), 6.80 (s, 2H).

TLC: Rf 0.24, $CH_2Cl_2$/MeOH 9:1.

Mass Spec.: FAB 711.4 (M+H)$^+$, 733.2 (M+Na)$^+$, 749.3 (M+K)$^+$.

Elemental Analysis for $C_{31}H_{50}N_8O_{11} \cdot 1.0H_2O$: Theoretical C, 51.09; H, 7.19; N, 15.38. Found C, 51.43; H, 7.00; N, 15.08.

EXAMPLE 24

Maleimidopropionylglutamyldi[β-Alanylhydrazide] (Compound No. 13a)

Maleimidopropionylglutamyldi[β-Alanyl(Boc)-hydrazide] (12a) (850 mg, 1.27 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 13a (890 mg, 100%)

$^1$H-NMR ($d_4$-Methanol): δ 1.83 and 2.02 (2m, 2H), 2.23 (t, 2H), 2.52 (q, 6H), 3.47 (m, 4H), 3.78 (m, 2H), 4.13 (dd, 1H), 6.82 (s, 2H).

Mass Spec.: FAB 469.0 (M+H)$^+$, 491.1 (M+Na)$^+$, 507.1 (M+K)$^+$.

Elemental Analysis for $C_{18}H_{28}N_8O_7 \cdot 3.75TFA \cdot 0.25Et_2O$: Theoretical C, 34.80; H, 3.77; N, 12.25. Found C, 34.63; H, 4.04; N, 12.20.

EXAMPLE 25

Maleimidobutyrylglutamyldi[β-Alanylhydrazide] (Compound No. 13b)

Maleimidobutyrylglutamyldi[β-Alanyl(Boc)-hydrazide] (12b) (800 mg, 1.17 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 13b (840 mg, 100%)

$^1$H-NMR ($d_4$-Methanol): δ 1.88 (m, 3H), 2.06 (m, 1H), 2.26 (t, 4H), 2.51 (t, 4H), 3.50 (m, 6H), 4.18 (dd, 1H), 6.82 (s, 2H).

Mass Spec.: FAB 483.2 $(M+H)^+$, 505.1 $(M+Na)^+$, 521.1 $(M+K)^+$.

Elemental Analysis for $C_{19}H_{30}N_8O_7 \cdot 3.5TFA \cdot 0.25Et_2O$: Theoretical C, 36.03; H, 4.03; N, 12.45. Found C, 36.00; H, 4.29; N, 12.26.

EXAMPLE 26

Maleimidocaproylglutamyldi[β-Alanylhydrazide] (Compound No. 13c)

Maleimidocaproylglutamyldi[β-Alanyl(Boc)-hydrazide] (12c) (800 mg, 1.13 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 13c (870 mg, 100%)

$^1$H-NMR ($d_4$-Methanol): δ 1.31 (p, 2H), 1.61 (s, 4H), 1.85 and 2.03 (2m, 2H), 2.24 (t, 4H), 2.50 (t, 4H), 3.47 (m, 6H), 4.19 (dd, 1H), 6.80 (s, 2H).

Mass Spec.: Ionspray 511.1 $(M+H)^+$, 533.0 $(M+Na)^+$.

Elemental Analysis for $C_{21}H_{34}N_8O_7 \cdot 2.75TFA \cdot 0.25Et_2O$: Theoretical C, 39.20; H, 4.70; N, 13.30. Found C, 39.32; H, 4.58; N, 13.06.

EXAMPLE 27

Maleimidopropionylglutamyldi[β-Alanyl-hydrazone] of Doxorubicin (Compound No. 3a "MP-Glu-(β-Ala-DOX)$_2$")

Maleimidopropionylglutamyldi[β-Alanyl-hydrazide] ditrifluoroacetate (13a) (1.0 g, 1.44 mmole) and DOX.HCl (1.68 g, 2.88 mmole) were dissolved in 600 ml methanol over a period of 3 hours. The reaction was concentrated to 100 ml by rotary evaporation, then stirred for 1 day. After further concentration to 10 ml, elution on an LH-20 column (2"×10") with methanol/DMF (1:1) was carried out. The purified product was concentrated by rotary evaporation and precipitated by the addition of acetonitrile. The red solid was isolated by centrifugation and dried under high vacuum to yield 3a (450 mg, 20%).

$^1$H-NMR ($d_4$-Methanol): δ 1.29 (2bd, 6H), 4.04 (s, 6H), 6.80 (s, 2H), 7.5–8.0 (m, 6H).

Mass Spec.: Ionspray 1519.6 $(M+H)^+$, 1541.2 $(M+Na)^+$.

Elemental Analysis for $C_{72}H_{82}N_{10}O_{27} \cdot 2HCl \cdot 7H_2O$: Theoretical C, 50.32; H, 5.75; N, 8.15. Found C, 50.20; H, 5.49; N, 8.44.

EXAMPLE 28

Maleimidobutyrylglutamyldi[β-Alanylhydrazone] of Doxorubicin (Compound No. 3b "MB-Glu-(β-Ala-DOX)$_2$")

Maleimidobutyrylglutamyldi[β-Alanylhydrazide] ditrifluoroacetate (13b) (280 mg, 0.395 mmole) and DOX.HCl (458 mg, 0.790 mmole) were dissolved in 250 ml methanol over a period of 3 hours. The reaction was concentrated to 50 ml by rotary evaporation, then stirred for 2 days. After further concentration to 5 ml, elution on an LH-20 column (1"×15") with methanol/DMF (1:1) was carried out. The purified product was concentrated by rotary evaporation and precipitated by the addition of acetonitrile. The red solid was isolated by centrifugation and dried under high vacuum to yield 3b (325 mg, 51%).

$^1$H-NMR ($d_4$-Methanol): δ 1.30 (m, 6H), 4.04 (s, 6H), 6.78 (s, 2H), 7.4–8.0 (m, 6H).

Mass Spec.: FAB 1533.7 $(M+H)^+$, 1555.5 $(M+Na)^+$, 1572.4 $(M+K)^+$.

Elemental Analysis for $C_{73}H_{84}N_{10}O_{27} \cdot 2HCl \cdot 7H_2O$: Theoretical C, 50.61; H, 5.82; N, 8.08. Found C, 50.83; H, 5.60; N, 7.41.

EXAMPLE 29

Maleimidocaproylglutamyldi[β-Alanylhydrazone] of Doxorubicin (Compound No. 3c "MC-Glu-(β-Ala-DOX)$_2$")

Maleimidocaproylglutamyldi[β-Alanylhydrazide] ditrifluoroacetate (13c) (148 mg, 0.20 mmole) and DOX.HCl (232 mg, 0.40 mmole) were dissolved in 150 ml methanol over a period of 3 hours. The reaction was concentrated to 10 ml by rotary evaporation, then stirred for 2 days. After further concentration to 2 ml, elution on an LH-20 column (1"×10") with methanol/DMF (1:1) was carried out. The purified product was concentrated by rotary evaporation and precipitated by the addition of acetonitrile. The red solid was isolated by centrifugation and dried under high vacuum to yield 3c (162 mg, 50%).

$^1$H-NMR (d6-DMSO): δ 1.20 (m, 6H), 4.0 (ppm) 6H, 6.95 (s, 2H), 7.5–8.1 (m, 6H).

Mass Spec.: FAB 1561 $(M+H)^+$, 1583.4 $(M+Na)^+$, 1599.9 $(M+K)^+$.

Elemental Analysis for $C_{75}H_{88}N_{10}O_7 \cdot 2HCl \cdot 7H_2O$: Theoretical C, 51.17; H, 5.95; N, 7.96. Found C, 51.04; H, 5.41; N, 10.23.

EXAMPLE 30

Z-Glutamyldi[glutamyldi(Boc)hydrazide] (Compound No. 14)

Z-Glutamic acid (844 mg, 3.0 mmole) and N-hydroxy succinimide (691 mg, 6.0 mmole) were dissolved in 6 ml DMF at 0° C. under dry $N_2$. A 0.5M solution of dicyclohexylcarbodiimide in methylene chloride (12.0 ml, 6.0 mmole) was added. The reaction was stirred for 4 hr. Dicyclohexylurea precipitate was filtered, and the filtrate was added to 5 (2.253 g, 6.0 mmole). After stirring at room temperature for 60 hr., the reaction was rotary evaporated to an oil, which was redissolved in 200 ml ethyl acetate. The organic layer was extracted three times with 125 ml 10% citric acid, 3 times with 125 ml saturated aqueous sodium bicarbonate, and once with 125 ml brine. The organic layer was dried over sodium sulfate and rotary evaporated to a foam. Flash chromatography was carried out on silica gel (2 in.×12 in.) with $CH_2Cl_2$/methanol/acetic acid 93:5:2. Pure fractions containing product (14) were pooled and concentrated to a foam by rotary evaporation to yield, after drying under high vacuum, 2.30 g (77%).

$^1$H-NMR ($d_4$-Methanol): δ 1.35 (s, 36H), 1.7–2.4 (m, 12H), 3.90 (bt, 1H), 4.35 (m, 2H), 4.98 (q[AB], 2H), 7.25 (m, 5H).

TLC: Rf 0.61, $CH_2Cl_2$/MeOH 9:1.

Mass Spec.: FAB 1018.5 $(M+Na)^+$, 1034.4 $(M+K)^+$.

Elemental Analysis for $C_{43}H_{69}N_{11}O_{16}$·$2H_2O$: Theoretical C, 50.04; H, 7.13; N, 14.93. Found C, 50.20; H, 6.85; N, 14.90.

EXAMPLE 31

Glutamyldi[glutamyldi(Boc)hydrazide] (Compound No. 15)

Z-Glutamyldi[glutamyldi(Boc)hydrazide] (14) (1.86 g, 1.87 mmole) was hydrogenated along with 1 g 10% Pd-C in 75 ml MeOH at 50 psi for 3 hr. The reaction was filtered through Celite and rotary evaporated. The resulting foam was dried under high vacuum to yield 15 (1.59 g, 99%).

$^1$H-NMR ($d_4$-Methanol): δ 1.46 (s, 36H), 1.6–2.4 (m, 12H), 3.23 (m, 1H), 4.40 (2t, 2H).

Mass Spec.: FAB 862 $(M+H)^+$, 884 $(M+Na)^+$, 900 $(M+K)^+$.

Elemental Analysis for $C_{35}H_{63}N_{11}O_{14}$·$1H_2O$: Theoretical C, 47.77; H, 7.45; N, 17.51. Found C, 47.67; H, 7.28; N, 17.33.

EXAMPLE 32

Maleimidopropionylglutamyldi[glutamyldi(Boc) hydrazide] (Compound No. 16a)

The N-hydroxysuccinimide ester of maleimidopropionic acid (300 mg, 1.13 mmole) was prepared as in the synthesis of 6a, then stirred with glutamyldi[glutamyldi(Boc) hydrazide] (15) (883 mg, 1.02 mmole) and triethylamine (143 ul, 1.02 mmole) in 25 ml DMF at room temperature for 16 hr. Solvent was removed by rotary evaporation, and the residue was purified by flash chromatography on silica gel (1 in.×10 in.) with $CH_2Cl_2$-acetic acid-methanol 93:2:5. Pure fractions were pooled, rotary evaporated, and dried under high vacuum to give 16a (400 mg, 39%).

$^1$H-NMR ($d_4$-Methanol): δ 1.46 (s, 36H), 1.8–2.4 (m, 12H), 2.50 (t, 2H), 3.76 (t, 2H), 4.11 (m, 1H), 4.39 (2t, 2H), 6.81 (s, 2H).

Mass Spec.: FAB 1035.6 $(M+Na)^+$, 1051 $(M+K)^+$.

EXAMPLE 33

Maleimidobutyrylglutamyldi[glutamyldi(Boc) hydrazide] (Compound No. 16b)

Maleimidobutyric acid (227 mg, 1.24 mmole) was dissolved with N-methylmorpholine (178 ul, 1.61 mmole) in 10 ml dry THF under $N_2$ at 0° C. Isobutylchloroformate (144 ul, 1.11 mmole) was added, followed 5 minutes later by the addition of glutamyldi[glutamyldi(Boc)hydrazide] (15) (960 mg, 1.11 mmole) as a solution in 15 ml DMF. The reaction was stored at 4° C. for 16 hours. The reaction was concentrated by rotary evaporation, then dissolved in 200 ml EtOAc. The organic layer was washed three times with 50 ml 10% citric acid, three times with 50 ml saturated $NaHCO_3$, and three times with 50 ml $H_2O$. The organic layer was concentrated to a foam, which was purified by flash chromatography on silica gel (1 in.×12 in.) with $CH_2Cl_2$-acetic acid-methanol 93:2:5. Pure fractions were pooled and rotary evaporated to a foam. Drying under high vacuum yielded 16b (900 mg, 79%).

$^1$H-NMR ($d_4$-Methanol): δ 1.46 (s, 36H), overlapping signals 1.86 (t), 2.22 (t), and 1.9–2.4 (m) 16H total, 3.50 (t, 2H), 4.11 (m, 1H), 4.40 (2t, 2H), 6.82 (s, 2H).

Mass Spec.: FAB 1049.5 $(M+Na)^+$, 1065.4 $(M+K)^+$.

Elemental Analysis for $C_{43}H_{70}N_{12}O_{17}$·$3.5H_2O$·3HOAc: Theoretical C, 46.33; H, 7.06; N, 13.23. Found C, 46.24; H, 6.52; N, 13.37.

EXAMPLE 34

Maleimidocaproylglutamyldi[glutamyldi(Boc) hydrazide] (Compound No. 16c)

This compound was synthesized following the procedure used for 16b. Yield of 16c was 330 mg, 54%.

$^1$H-NMR ($d_4$-Methanol): δ 1.28 (m, 2H), 1.46 (s, 36H), 1.56 (m, 4H), overlapping signals 1.9–2.5 (m) and 2.20 (t) 14H total, 3.48 (t, 2H), 4.10 (m, 1H), 4.40 (m, 2H), 6.80 (s, 2H).

Mass Spec.: FAB 1078.8 $(M+Na)^+$, 1093.5 $(M+K)^+$.

Elemental Analysis for $C_{45}H_{74}N_{12}O_{17}$·$3H_2O$·3HOAc: Theoretical C, 47.51; H, 7.19; N, 13.04. Found C, 47.44; H, 6.48; N, 13.14.

EXAMPLE 35

Maleimidopropionylglutamyldi[glutamyldi-hydrazide] (Compound No. 17a)

Maleimidopropionylglutamyldi[glutamyldi(Boc) hydrazide] (16a) (400 mg, 0.395 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 17a (250 mg, 59%).

$^1$H-NMR ($d_4$-Methanol) of the crude material verified complete removal of the BOC groups. This was used in the synthesis of 18a without further purification.

EXAMPLE 36

Maleimidobutyrylglutamyldi[glutamyl-dihydrazide] (Compound No. 17b)

Maleimidobutyrylglutamyldi[glutamyldi(Boc)-hydrazide] (16b) (900 mg, 0.877 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 17b (817 mg, 86%)

$^1$H-NMR ($d_4$-Methanol): δ overlapping signals 1.7–2.5 (m), 1.80 (t), and 2.17 (t) total 16H, 3.45 (t, 2H), 4.04 (t, 1H), 4.36 (m, 2H), 6.75 (s, 2H).

Elemental Analysis for $C_{23}H_{38}N_{12}O_9$·6.5 TFA: Theoretical C, 31.61; H, 3.28; N, 12.29. Found C, 31.76; H, 3.49; N, 12.06.

EXAMPLE 37

Maleimidocaproylglutamyldi[glutamyl-dihydrazide] (Compound No. 17c)

Maleimidocaproylglutamyldi[glutamyldi(Boc)-hydrazide] (16c) (330 mg, 0.313 mmole) was stirred in 15 ml $CH_2Cl_2$/trifluoroacetic acid (1:1) under $N_2$ for 1.5 hr. Solvents were removed by rotary evaporation. Ether was added and co-evaporated three times, then the resulting solid was triturated with ether. The solid was filtered and dried under high vacuum to yield 17c (350 mg, 100%)

$^1$H-NMR ($d_4$-Methanol): δ 1.30 (m, 2H), 1.60 (2t, 4H), overlapping signals 1.9–2.5 (m) and 2.22 (t) total 14H, 3.47 (t, 2H), 4.09 (t, 1H), 4.43 (2t, 2H), 6.80 (s, 2H).

Elemental Analysis for $C_{25}H_{42}N_{12}O_9 \cdot 6.2$ TFA: Theoretical C, 32.99; H, 3.57; N, 12.34. Found C, 32.76; H, 3.73; N, 12.72.

EXAMPLE 38

Maleimidopropionylglutamyldi[glutamyl-dihydrazone] of Doxorubicin (Compound No. 18a)

Maleimidopropionylglutamyldi[glutamyl-dihydrazide] (17a) (250 mg, 0.230 mmole) and DOX.HCl (588 mg, 1.01 mmole) were dissolved in 100 ml methanol then concentrated to 25 ml by rotary evaporation and stirred for 2 days. The reaction was further concentrated to 15 ml and eluted on an LH-20 column (1"×10") with methanol. The purified product was rotary evaporated to a red film and dried under high vacuum to yield 18a (180 mg, 27%).

$^1$H-NMR ($d_4$-Methanol): (selected peaks) δ 1.33 (m, 12H), 4.04 and 4.06 (2d, 12H), 6.72 (s, 2H), 7.4–8.0 (m, 12H).

Mass Spec.: FAB Ionspray 2713.5 $(M+H)^+$.

Elemental Analysis for $C_{130}H_{144}N_{16}O_{49} \cdot 4HCl \cdot 4H_2O \cdot 4$ TFA: Theoretical C, 48.91; H, 4.76; N, 6.61. Found C, 48.49; H, 5.28; N, 7.06.

EXAMPLE 39

Maleimidobutyrylglutamyldi[glutamyl-dihydrazone] of Doxorubicin (Compound No. 18b)

Maleimidobutyrylglutamyldi[glutamyl-dihydrazide] (17b) (300 mg, 0.273 mmole) and DOX.HCl (697 mg, 1.20 mmole) were dissolved in 100 ml methanol then concentrated to 25 ml by rotary evaporation and stirred for 2 days. The reaction was further concentrated to 15 ml and eluted on an LH-20 column (1"×10") with methanol. The purified product was rotary evaporated to a red film and dried under high vacuum to yield 18b (500 mg, 64%).

$^1$H-NMR ($d_4$-Methanol): (selected peaks) δ 1.36 (m, 12H), 4.04 and 4.10 (2d, 12H), 6.69 (s, 2H), 7.5–8.0 (m, 12H).

Mass Spec.: FAB Ionspray 2728 $(M+H)^+$.

Elemental Analysis for $C_{131}H_{146}N_{16}O_{49} \cdot 4HCl \cdot 2$ TFA.$4H_2O$: Theoretical C, 51.08; H, 5.08; N, 7.06. Found C, 51.02; H, 5.05; N, 7.16.

EXAMPLE 40

Maleimidocaproylglutamyldi[glutamyl-dihydrazone] of Doxorubicin (Compound No. 18c "MC-Glu $(DOX)_4$")

Maleimidocaproylglutamyldi[glutamyl-dihydrazide] (17c) (233 mg, 0.210 mmole) and DOX.HCl (489 mg, 0.843 mmole) were dissolved in 100 ml methanol then concentrated to 25 ml by rotary evaporation and stirred for 2 days. The reaction was further concentrated to 15 ml and eluted on an LH-20 column (1"×10") with methanol. The purified product was rotary evaporated to a red film and dried under high vacuum to yield 18c (430 mg, 71%).

$^1$H-NMR ($d_4$-Methanol): (selected peaks) δ 1.36 (m, 12H), 4.04 and 4.10 (2d, 12H), 6.69 (s, 2H), 7.5–8.0 (m, 12H).

Mass Spec.: FAB Ionspray 1379 $(M+H)^{2+}$.

Elemental Analysis for $C_{133}H_{150}N_{16}O_{49} \cdot 4HCl \cdot 4TFA \cdot 4H_2O$: Theoretical C, 49.36; H, 4.88; N, 6.53. Found C, 49.34; H, 4.79; N, 6.66.

EXAMPLE 41

Compound No. 19

Z—$NHCH_2CH_2$—Br (3.16 g, 12.3 mmole) and (BOC—$NHCH_2CH_2)_2$—NH (3.72 g, 12.3 mmole) were stirred in 60 ml ACN/40 ml phosphate buffer (0.1M, pH 9) at 55° C. for 2 days. After cooling, the reaction was diluted with 200 ml $H_2O$ and extracted twice with 200 ml $Et_2O$. The organic layers were combined, dried over $Na_2SO_4$, and evaporated under vacuum. The oily residue was chromatographed on Merck silica gel 60 (2"×11") with (1) $CH_2Cl_2$, 2 L, (2) $CH_2Cl_2$/MeOH 97.5:2.5, 1.5 L, and (3) $CH_2Cl_2$/MeOH 95:5, 2 L. The desired product 19, which elutes in (2)–(3), was pooled, evaporated under vacuum, and dried under high vacuum to yield 1.93 g (33%).

$^1$H-NMR ($CDCl_3$): δ 1.37 (s, 18H), 2.47 (m, 6H), 3.15 (m, 6H), 5.07 (s, 2H), 7.28 (m, 5H).

$^{13}$C-NMR ($CDCl_3$): δ 28.38, 38.55, 39.01, 53.90, 54.27, 65.18, 66.60, 79.29, 126.94, 127.50, 127.96, 128.14, 128.41, 128.47, 136.66, 156.38, 156.78.

Mass Spec.: FAB 481.2 $(MH^+)$

Elemental Analysis for $C_{24}H_{40}N_4O_6$: Theoretical C, 59.98; H, 8.39; N, 11.66. Found C, 60.26; H, 8.43; N, 11.60.

FTIR: 3336, 2976, 1694, 1524, 1366, 1252, 1170, 736, 698 $cm^{-1}$.

EXAMPLE 42

Compound No. 20

19 (1.92 g, 3.99 mmole) was stirred in 50% TFA/$CH_2Cl_2$ (60 ml) for 3 hr. Solvents were removed by rotary evaporation, then repeated co-evaporations with $Et_2O$. The oily product was triturated with 50 ml $Et_2O$ three times, then dried under high vacuum to yield 20 as a foam (2.29 g, 100%).

$^1$H-NMR ($d^4$-MeOH): δ 2.64 (t, 2H), 2.78 (t, 4H), 3.01 (t, 4H), 3.21 (t, 2H), 5.08 (s, 2H), 7.34 (m, 5H).

$^{13}$C-NMR ($d^4$-MeOH): δ 38.36, 39.53, 52.61, 54.95, 67.69, 128.91, 129.12, 129.51, 138.2, 159.2.

Mass Spec.: FAB 281.1 $(MH^+)$

High Res. Mass Spec.: Theoretical, 281.1977; Experimental, 281.1984 $(MH^+)$.

Elemental Analysis for $C_{14}H_{24}N_4O_2 \cdot 2.6TFA$: Theoretical C, 39.98; H, 4.65; N, 9.71; F, 25.69. Found C, 39.85; H, 4.60; N, 9.68; F, 25.38.

FTIR: 3036, 1680, 1532, 1260, 1204, 1136, 838, 800, 722 $cm^{-1}$.

EXAMPLE 43

Compound No. 21

$BrCH_2CONHNH$-BOC (10.12 g, 40.0 mmole) was added in several portions over a 5 minute period to a stirring suspension of 20 (6.22 g, 10.0 mmole) and $KHCO_3$ (8.01 g, 80 mmole) in 100 ml DMF at 0° C. The reaction was then stirred at room temperature for 60 hours. Solvents were removed by rotary evaporation to an oily residue. This was dissolved in 500 ml of Et$_2$O/EtOAc 1:1 and extracted 5 times with 150 ml saturated NaHCO$_3$ followed by two times with water. The organic layer was dried over Na$_2$SO$_4$ and rotary evaporated to an oil. Further drying under high vacuum yielded 21 (9.67 g, 100%).

$^1$H-NMR (d$^4$-MeOH): δ 1.45 (s, 36H), 2.69 (m, 10H), 3.23 (t, 2H), 3.37 (s, 8H), 5.06 (s, 2H), 7.33 (m, 5H).

$^{13}$C-NMR (d$^4$-MeOH): δ 28.64, 53.28, 53.88, 54.56, 58.59, 66.92, 67.54, 81.94, 129.07, 129.51, 138.35, 157.63, 158.89, 173.20.

Mass Spec.: Ionspray 969.6 (MH$^+$)

Elemental Analysis for C$_{42}$H$_{72}$N$_{12}$O$_{14}$·0.5H$_2$O: Theoretical C, 51.57; H, 7.52; N, 17.18. Found C, 51.73; H, 7.52; N, 16.84.

FTIR: 3296, 2980, 1728, 1696, 1518, 1394, 1368, 1248, 1162, 1048, 1016, 874, 756, 698 cm$^{-1}$.

EXAMPLE 44

Compound No. 22

21 (2.11 g, 2.18 mmole) was hydrogenated at 35 psi in 50 ml MeOH for 2 hours. The reaction was filtered through Celite, rotary evaporated, and dried under high vacuum to yield 22 as a foam (1.65 g, 91%).

$^1$H-NMR (d$^4$-MeOH): δ 1.46 (s, 36H), 2.71 (m, 12H), 3.34 (s, 8H).

$^{13}$C-NMR (d$^4$-MeOH): δ 28.64, 34.77, 53.11, 53.91, 58.12, 81.90, 157.64, 172.88.

Mass Spec.: Ionspray 835.5 (MH$^+$).

Elemental Analysis for C$_{34}$H$_{66}$N$_{12}$O$_{12}$·1.0H$_2$O·1.0MeOH: Theoretical C, 47.50; H, 8.20; N, 18.99. Found C, 47.41; H, 7.88; N, 18.74.

FTIR: 3292, 2980, 1720, 1690, 1484, 1368, 1248, 1162, 1048, 1016, 880, 773, 574 cm$^{-1}$.

EXAMPLE 45

Compound No. 23

A solution of 22 (1.03 g, 1.23 mmole) and maleic anhydride (121 mg, 1.23 mmole) was stirred in 25 ml CH$_2$Cl$_2$ for 2.5 hours. Solvents were removed by rotary evaporation to yield 23 (1.16 g, 100%).

$^1$H-NMR (d$^4$-MeOH): δ 1.45 (s, 36H), 3.13 (m, 4H), 3.45 (m and s, 16H), 3.68 (m, 2H), 6.17 (dd, 2H).

Mass Spec.: Ionspray 933.6 (MH$^+$), 955.5 (M+Na$^+$).

EXAMPLE 46

Compound No. 24

23 (603 mg, 0.646 mmole) and EDCI (149 mg, 0.775 mmole) were stirred in 25 ml dry CH$_2$Cl$_2$ under N$_2$ for 2.5 hr. at room temperature. The reaction was then extracted three times with 25 ml saturated aqueous NaHCO$_3$ solution, then once with 25 ml water. The organic layer was dried over Na$_2$SO$_4$, rotary evaporated, and dried under high vacuum to yield the isomaleimide intermediate (494 mg, 84%).

$^1$H-NMR (CDCl$_3$): δ 1.45 (s, 36H), 2.8 (m, 10H), 3.31 (s, 8H), 3.7 (m, 2H), 6.57 and 7.40 (dd, 2H).

This product was stirred with HOBt (35 mg, 0.259 mmole) in 8 ml DMF for 7 hours at room temperature. Solvent was removed by rotary evaporation. The oily residue was dissolved in 60 ml Et2O/EtOAc 1:1 and extracted five times with 25 ml saturated aqueous NaHCO$_3$ solution, then once with 25 ml water. The organic layer was dried over Na$_2$SO$_4$, rotary evaporated, and dried under high vacuum to yield the maleimide product 24 (463 mg, 94%).

$^1$H-NMR (CDCl$_3$): δ 1.45 (s, 36H), 2.7 (m, 10H), 3.32 (s, 8H), 3.57 (m, 2H), 6.68 (s, 2H).

$^{13}$C-NMR (CDCl$_3$): δ 28.16, 81.73, 134.25, 155.5, 170.79.

Mass Spec.: Electrospray 915.5 (MH$^+$), 937.5 (M+Na$^+$).

FTIR: 3300, 2982, 1738, 1708, 1680 (sh), 1498, 1394, 1368, 1248, 1162, 1048, 1016, 72, 696 cm$^{-1}$.

EXAMPLE 47

Compound No. 25

24 (214 mg, 0.234 mmole) was stirred with p-toluenesulfonic acid (450 mg, 2.37 mmole) in 25 ml dry CH$_2$Cl$_2$ under N$_2$ for 3 hours. Solvent was removed by rotary evaporation. The residue was triturated four times with 125 ml Et$_2$O, then dried under high vacuum to yield 25 (378 mg, 94%).

$^1$H-NMR (d$^4$-MeOH): δ 2.36 (s, 21H), 3.22 (t, 2H), 3.52 (m, 8H), 3.71 (s, 8H), 3.94 (t, 2H), 6.85 (s, 2H), 7.23 (d, 14H), 7.70 (d, 14H).

Mass Spec.: FAB 515.1 (MH$^+$).

EXAMPLE 48

Compound No. 26

25 (100 mg, 58 umole) and Doxorubicin HCl (177 mg, 305 umole) were stirred in 25 ml dry methanol for 24 hour. The reaction was concentrated by rotary evaporation to 4 ml, then purified on Sephadex LH-20 (1"×18") with methanol. Fractions containing pure product were pooled, rotary evaporated, and dried under high vacuum to yield 26 (113 mg, 59%).

$^1$H-NMR (d$^4$-MeOH): δ 1.2 (m, 12H), 3.9 (s, 12H), 6.8 (s, 2H), 7.2–8.0 (m) superimposed with 7.2 (d), and 7.7 (d) total 24 H.

EXAMPLE 49

Compound No. 27

Mono-Z-ethylene diamine HCl (3.46 g, 15 mmole), BrCH$_2$CONHNH-BOC (7.59 g, 30 mmole), and KHCO$_3$ (5.26 g, 52.5 mmole) were stirred in 60 ml DMF under N$_2$ at room temperature for 24 hours. The reaction was partitioned between 25 ml Et$_2$O and 150 ml saturated aqueous NaHCO$_3$. The Et$_2$O layer was washed with 100 ml saturated aqueous NaHCO$_3$. All aqueous layers were extracted with 100 ml Et$_2$O. The combined Et$_2$O layers were washed with brine, dried over Na$_2$SO$_4$, and rotary evaporated to yield 6.5 g crude product. This material was flash chromatographed on 2"×20" silica gel 60 (Merck) column with (1) CH$_2$Cl$_2$/MeOH 95:5, 2 L, (2) CH$_2$Cl$_2$/MeOH 92.5:7.5, 1 L, and (3) CH$_2$Cl$_2$/MeOH 90:10, 2 L. Fractions containing the desired product were pooled, rotary evaporated, and dried under high vacuum to yield 27 as a foam (4.64 g, 57%).

$^1$H-NMR (CDCl$_3$): δ 1.36 (s, 18H), 2.70 (m, 2H), 3.22 (s, 4H), 3.28 (m, 2H), 5.01 (s, 2H), 7.25 (m, 5H).

$^{13}$C-NMR (CDCl$_3$): δ 28.08, 38.75, 55.67, 57.19, 66.77, 81.85, 128.02, 128.41, 136.47, 155.95, 158.10, 170.79.

Mass Spec.: Ionspray 539.3 (MH$^+$), 561.2 (M+Na$^+$), 577.1 (M+K$^+$).

Elemental Analysis for $C_{24}H_{38}N_6O_8 \cdot 0.5H_2O$: Theoretical C, 52.64; H, 7.18; N, 15.35. Found C, 52.53; H, 7.05; N, 15.30.

FTIR: 3300, 2980, 1724, 1694, 1528, 1368, 1250, 1160, 1016, 880, 754, 698 $cm^{-1}$.

EXAMPLE 50

Compound No. 28

27 was hydrogenated in 100 ml EtOH along with 2 g 10% Pd-C at 45 psi for 4.5 hours. After filtration of the catalyst through Celite, the solvent was rotary evaporated and dried under high vacuum to yield 28 as a foam (3.06 g, 92%).

$^1$H-NMR (CDCl3): δ 1.43 and 1.44 (2s, 18H), 2.80 (t, 2H), 3.23 (d, 4H), 3.39 (m, 2H). ($d^4$-MeOH): 1.24 and 1.26 (2s, 18H), 2.59 (t, 2H), 3.02 (d, 4H), 3.15 (t, 2H).

Mass Spec.: Ionspray 405.3 ($MH^+$).

Elemental Analysis for $C_{16}H_{32}N_6O_6 \cdot 0.5H_2O$: Theoretical C, 46.48; H, 8.04; N, 20.33. Found C, 46.57; H, 8.04; N, 20.37.

FTIR: 3328, 2980, 1698, 1672, 1500, 1368, 1300, 1252, 1162, 778, 692 $cm^{-1}$.

EXAMPLE 51

Compound No. 29

Maleic anhydride (98 mg, 1.0 mmole) and 28 (405 mg, 1.0 mmole) were stirred in 15 ml $CH_2Cl_2$ for 2 hours at room temperature. The reaction was rotary evaporated, and the crude product triturated with $Et_2O$. The residue was dried under high vacuum, yielding 29 (400 mg, 80%).

$^1$H-NMR (CDCl$_3$): δ 1.47 and 1.48 (2s, 18H), 2.89 (t, 2H), 3.32 (d, 4H), 3.46 (m, 2H), 6.42 (dd, 2H).

EXAMPLE 52

Compound No. 30

29 (503 mg, 1.0 mmole) and EDCI (230 mg, 1.2 mmole) are stirred in 25 ml dry $CH_2Cl_2$ under $N_2$ for 2.5 hr. at room temperature. The reaction is then extracted three times with 25 ml saturated aqueous $NaHCO_3$ solution, then once with 25 ml water. The organic layer is dried over $Na_2SO_4$, rotary evaporated, and dried under high vacuum to yield the isomaleimide intermediate.

This product is stirred with HOBt (54 mg, 0.40 mmole) in 8 ml DMF for 7 hours at room temperature. Solvent is removed by rotary evaporation. The oily residue is dissolved in 60 ml $Et_2O$/EtOAc 1:1 and extracted five times with 25 ml saturated aqueous $NaHCO_3$ solution, then once with 25 ml water. The organic layer is dried over $Na_2SO_4$, rotary evaporated, and dried under high vacuum to yield the maleimide product 30 (455 mg, 94%).

EXAMPLE 53

Compound No. 31

30 (485 mg, 1.0 mmole) is stirred with p-toluenesulfonic acid (1.90 g, 10 mmole) in 50 ml dry $CH_2Cl_2$ under $N_2$ for 3 hours. Solvent is removed by rotary evaporation. The residue is triturated four times with 125 ml $Et_2O$, then dried under high vacuum to yield 31 (800 mg, 94%).

EXAMPLE 54

Compound No. 32

31 (200 mg, 0.25 mmole) and Doxorubicin HCl (377 mg, 0.65 mmole) are stirred in 25 ml dry methanol for 24 hour. The reaction is concentrated by rotary evaporation to 4 ml, then purified in two equal portions on Sephadex LH-20 (1"×18") with methanol. Fractions containing pure product are pooled, rotary evaporated, and dried under high vacuum to yield 32 (200 mg, 50%).

EXAMPLE 55

Compound No. 33 t-Butyl carbazate (396 mg, 3 mmole) is stirred in 10 ml dry $CH_2Cl_2$ under $N_2$, then triethylamine (0.6 g, 6 mmole) is added followed by triphosgene (296 mg, 1 mmole) in a single portion. When the initial reaction subsides, 20 (934 mg, 1.5 mmole) is added in 20 ml $CH_2Cl_2$ along with additional triethylamine (0.45 g, 4.5 mmole). The mixture is stirred at room temperature for 1.5 hr., diluted with $CH_2Cl_2$, then partitioned with water (100 ml). The organic layer is dried over $Na_2SO_4$, and rotary evaporated. Flash chromatography on silica gel 60 yields pure product 33 (684 mg, 50%).

EXAMPLE 56

Compound No. 34

33 (650 mg, 0.71 mmole) is hydrogenated in 50 ml EtOH along with 1 g 10% Pd-C at 45 psi for 4.5 hours. After filtration of the catalyst through Celite, the solvent is rotary evaporated and dried under high vacuum to yield 34 as a foam (550 mg, 100%).

EXAMPLE 57

Compound No. 35

Maleic anhydride (63 mg, 0.64 mmole) and 34 (500 mg, 0.64 mmole) are stirred in 15 ml $CH_2Cl_2$ for 2 hours at room temperature. The reaction is rotary evaporated, and the crude product triturated with $Et_2O$. The residue is dried under high vacuum, yielding 35 (448 mg, 80%).

EXAMPLE 58

Compound No. 36

35 (438 mg, 0.5 mmole) and EDCI (115 mg, 0.6 mmole) are stirred in 25 ml dry $CH_2Cl_2$ under $N_2$ for 2.5 hr. at room temperature. The reaction is then extracted three times with 25 ml saturated aqueous $NaHCO_3$ solution, then once with 25 ml water. The organic layer is dried over $Na_2SO_4$, rotary evaporated, and dried under high vacuum to yield the isomaleimide intermediate.

This product is stirred with HOBt (27 mg, 0.20 mmole) in 8 ml DMF for 7 hours at room temperature. Solvent is removed by rotary evaporation. The oily residue is dissolved in 60 ml $Et_2O$/EtOAc 1:1 and extracted five times with 25 ml saturated aqueous $NaHCO_3$ solution, then once with 25 ml water. The organic layer is dried over $Na_2SO_4$, rotary evaporated, and dried under high vacuum to yield the maleimide product 36 (400 mg, 94%).

EXAMPLE 59

Compound No. 37

36 (400 mg, 0.47 mmole) is stirred with p-toluenesulfonic acid (894 mg, 4.7 mmole) in 50 ml dry $CH_2Cl_2$ under $N_2$ for 3 hours. Solvent is removed by rotary evaporation. The residue is triturated four times with 125 ml $Et_2O$, then dried under high vacuum to yield 37 (455 mg, 94%).

EXAMPLE 60

Compound No. 38

37 (257 mg, 0.25 mmole) and Doxorubicin HCl (377 mg, 0.65 mmole) are stirred in 25 ml dry methanol for 24 hour. The reaction is concentrated by rotary evaporation to 4 ml, then purified in two equal portions on Sephadex LH-20 (1"×18") with methanol. Fractions containing pure product are pooled, rotary evaporated, and dried under high vacuum to yield 38 (222 mg, 50%).

EXAMPLE 61

Compound No. 39

Z—NHCH$_2$CH$_2$—Br (3.16 g, 12.3 mmole) and (BOC—NHCH$_2$CH$_2$)$_2$—NH (3.72 g, 12.3 mmole) were stirred in 60 ml ACN/40 ml phosphate buffer (0.1M, pH 9) at 55° C. for 2 days. After cooling, the reaction was diluted with 200 ml H$_2$O and extracted twice with 200 ml Et$_2$O. The organic layers were combined, dried over Na$_2$SO$_4$, and evaporated under vacuum. The oily residue was chromatographed on Merck silica gel 60 (2"×11") with (1) CH$_2$Cl$_2$, 2 L, (2) CH$_2$Cl$_2$/MeOH 97.5:2.5, 1.5 L, and (3) CH$_2$Cl$_2$/MeOH 95:5, 2 L. The desired product 102, which elutes in (2)–(3), was pooled, evaporated under vacuum, and dried under high vacuum to yield 1.93 g (33%).

$^1$H-NMR (CDCl$_3$): δ 1.37 (s, 18H), 2.47 (m, 6H), 3.15 (m, 6H), 5.07 (s, 2H), 7.28 (m, 5H).

$^{13}$C-NMR (CDCl$_3$): δ 28.38, 38.55, 39.01, 53.90, 54.27, 65.18, 66.60, 79.29, 126.94, 127.50, 127.96, 128.14, 128.41, 128.47, 136.66, 156.38, 156.78.

Mass Spec.: FAB 481.2 (MH$^+$)

Elemental Analysis for C$_{24}$H$_{40}$N$_4$O$_6$: Theoretical C, 59.98; H, 8.39; N, 11.66. Found C, 60.26; H, 8.43; N, 11.60.

FTIR: 3336, 2976, 1694, 1524, 1366, 1252, 1170, 736, 698 cm$^{-1}$.

EXAMPLE 62

Compound No. 40

102 (1.92 g, 3.99 mmole) was stirred in 50% TFA/CH$_2$Cl$_2$ (60 ml) for 3 hr. Solvents were removed by rotary evaporation, then repeated co-evaporations with Et$_2$O. The oily product was triturated with 50 ml Et$_2$O three times, then dried under high vacuum to yield 103 as a foam (2.29 g, 100%).

$^1$H-NMR (d$^4$-MeOH): δ 2.64 (t, 2H), 2.78 (t, 4H), 3.01 (t, 4H), 3.21 (t, 2H), 5.08 (s, 2H), 7.34 (m, 5H).

$^{13}$C-NMR (d$^4$-MeOH): δ 38.36, 39.53, 52.61, 54.95, 67.69, 128.91, 129.12, 129.51, 138.2, 159.2.

Mass Spec.: FAB 281.1 (MH$^+$)

High Res. Mass Spec.: Theoretical, 281.1977;

Experimental, 281.1984 (MH$^+$).

Elemental Analysis for C$_{14}$H$_{24}$N$_4$O$_2$.2.6TFA: Theoretical C, 39.98; H, 4.65; N, 9.71; F, 25.69. Found C, 39.85; H, 4.60; N, 9.68; F, 25.38.

FTIR: 3036, 1680, 1532, 1260, 1204, 1136, 838, 800, 722 cm$^{-1}$.

EXAMPLE 63

Compound No. 41

BrCH$_2$CONHNH-BOC (10.12 g, 40.0 mmole) was added in several portions over a 5 minute period to a stirring suspension of 103 (6.22 g, 10.0 mmole) and KHCO$_3$ (8.01 g, 80 mmole) in 100 ml DMF at 0° C. The reaction was then stirred at room temperature for 60 hours. Solvents were removed by rotary evaporation to an oily residue. This was dissolved in 500 ml of Et$_2$O/EtOAc 1:1 and extracted 5 times with 150 ml saturated NaHCO$_3$ followed by two times with water. The organic layer was dried over Na$_2$SO$_4$ and rotary evaporated to an oil. Further drying under high vacuum yielded 104 (9.67 g, 100%).

$^1$H-NMR (d$^4$-MeOH): δ 1.45 (s, 36H), 2.69 (m, 10H), 3.23 (t, 2H), 3.37 (s, 8H), 5.06 (s, 2H), 7.33 (m, 5H).

$^{13}$C-NMR (d$^4$-MeOH): δ 28.64, 53.28, 53.88, 54.56, 58.59, 66.92, 67.54, 81.94, 129.07, 129.51, 138.35, 157.63, 158.89, 173.20.

Mass Spec.: Ionspray 969.6 (MH$^+$)

Elemental Analysis for C$_{42}$H$_{72}$N$_{12}$O$_{14}$.0.5H$_2$O: Theoretical C, 51.57; H, 7.52; N, 17.18. Found C, 51.73; H, 7.52; N, 16.84.

FTIR: 3296, 2980, 1728, 1696, 1518, 1394, 1368, 1248, 1162, 1048, 1016, 874, 756, 698 cm$^{-1}$.

EXAMPLE 64

Compound No. 42

104 (2.11 g, 2.18 mmole) was hydrogenated at 35 psi in 50 ml MeOH for 2 hours. The reaction was filtered through Celite, rotary evaporated, and dried under high vacuum to yield 105 as a foam (1.65 g, 91%).

$^1$H-NMR (d$^4$-MeOH): δ 1.46 (s, 36H), 2.71 (m, 12H), 3.34 (s, 8H).

$^{13}$C-NMR (d$^4$-MeOH): δ 28.64, 34.77, 53.11, 53.91, 58.12, 81.90, 157.64, 172.88.

Mass Spec.: Ionspray 835.5 (MH$^+$).

Elemental Analysis for C$_{34}$H$_{66}$N$_{12}$O$_{12}$.1.0H$_2$O .1.0MeOH:

Theoretical C, 47.50; H, 8.20; N, 18.99. Found C, 47.41; H, 7.88; N, 18.74.

FTIR: 3292, 2980, 1720, 1690, 1484, 1368, 1248, 1162, 1048, 1016, 880, 773, 574 cm$^{-1}$.

EXAMPLE 65

Compound No. 43

A solution of 105 (1.03 g, 1.23 mmole) and maleic anhydride (121 mg, 1.23 mmole) was stirred in 25 ml CH$_2$Cl$_2$ for 2.5 hours. Solvents were removed by rotary evaporation to yield 106 (1.16 g, 100%).

$^1$H-NMR (d$^4$-MeOH): δ 1.45 (s, 36H), 3.13 (m, 4H), 3.45 (m and s, 16H), 3.68 (m, 2H), 6.17 (dd, 2H).

Mass Spec.: Ionspray 933.6 (MH$^+$), 955.5 (M+Na$^+$).

EXAMPLE 66

Compound No. 44

106 (603 mg, 0.646 mmole) and EDCI (149 mg, 0.775 mmole) were stirred in 25 ml dry CH$_2$Cl$_2$ under N$_2$ for 2.5 hr. at room temperature. The reaction was then extracted three times with 25 ml saturated aqueous NaHCO$_3$ solution, then once with 25 ml water. The organic layer was dried over Na$_2$SO$_4$, rotary evaporated, and dried under high vacuum to yield the isomaleimide intermediate (494 mg, 84%).

$^1$H-NMR (CDCl$_3$): δ 1.45 (s, 36H), 2.8 (m, 10H), 3.31 (s, 8H), 3.7 (m, 2H), 6.57 and 7.40 (dd, 2H).

This product was stirred with HOBt (35 mg, 0.259 mmole) in 8 ml DMF for 7 hours at room temperature. Solvent was removed by rotary evaporation. The oily residue was dissolved in 60 ml Et2O/EtOAc 1:1 and extracted five times with 25 ml saturated aqueous NaHCO3 solution, then once with 25 ml water. The organic layer was dried over $Na_2SO_4$, rotary evaporated, and dried under high vacuum to yield the maleimide product 107 (463 mg, 94%).

$^1$H-NMR (CDCl$_3$): δ 1.45 (s, 36H), 2.7 (m, 10H), 3.32 (s, 8H), 3.57 (m, 2H), 6.68 (s, 2H).

$^{13}$C-NMR (CDCl$_3$): δ 28.16, 81.73, 134.25, 155.5, 170.79.

Mass Spec.: Electrospray 915.5 (MH$^+$), 937.5 (M+Na$^+$).

FTIR: 3300, 2982, 1738, 1708, 1680 (sh), 1498, 1394, 1368, 1248, 1162, 1048, 1016, 72, 696 cm$^{-1}$.

EXAMPLE 67

Compound No. 45

107 (214 mg, 0.234 mmole) was stirred with p-toluenesulfonic acid (450 mg, 2.37 mmole) in 25 ml dry $CH_2Cl_2$ under $N_2$ for 3 hours. Solvent was removed by rotary evaporation. The residue was triturated four times with 125 ml Et$_2$O, then dried under high vacuum to yield 108 (378 mg, 94%).

$^1$H-NMR (d$^4$-MeOH): δ 2.36 (s, 21H), 3.22 (t, 2H), 3.52 (m, 8H), 3.71 (s, 8H), 3.94 (t, 2H), 6.85 (s, 2H), 7.23 (d, 14H), 7.70 (d, 14H).

Mass Spec.: FAB 515.1 (MH$^+$).

EXAMPLE 68

Compound No. 46

108 (100 mg, 58 umole) and Doxorubicin HCl (177 mg, 305 umole) were stirred in 25 ml dry methanol for 24 hour. The reaction was concentrated by rotary evaporation to 4 ml, then purified on Sephadex LH-20 (1"×18") with methanol. Fractions containing pure product were pooled, rotary evaporated, and dried under high vacuum to yield 109 (113 mg, 59%).

$^1$H-NMR (d$^4$-MeOH): δ 1.2 (m, 12H), 3.9 (s, 12H), 6.8 (s, 2H), 7.2–8.0 (m) superimposed with 7.2 (d), and 7.7 (d) total 24 H.

EXAMPLE 69

Conjugate Synthesis

Thiolation

Method A. On a scale ≦3 g, (see Willner, D., Trail, P. A., Hofstead, S. J., King, H. D., Lasch, Braslawsky, G. R., Greenfield, R. S., Kaneko, T., Firestone, R. A. (1993) (6-Maleimidocaproyl)-hydrazone of Doxorubicin:A new derivative for the preparation of immunoconjugates of Doxorubicin. *Bioconjugate Chem.*, 4, 521.) In typical example, 1.54 g BR96 (180 ml at 53.4 uM, 9.6 umole) was de-oxygenated by several cycles of alternating vacuum and Ar atmosphere. This was then treated with 34 mM DTT (2.0 ml, 68.0 umole in Ar-bubbled PBS, pH 7.0) and stirred at 37° C. under Ar for 3 hr. Removal of low molecular weight compounds was accomplished by ultrafiltration against PBS, pH 7.0 in an Amicon stirred cell at 4° C. A 400 ml Amicon cell was fitted with an Amicon YM30 filter (molecular weight cut-off 30,000), and charged to 40 psi with Ar. Cell eluant was monitored for thiol content with Ellman's reagent until a baseline reading at 412 nm was obtained. Concentration of protein and thiol groups were determined according to the previously reported method. In this example, 1.47 g reduced BR96 (190 ml at 48.57 uM MAb, 412.7 uM thiol) was obtained, for a yield of 95% and a thiol titer of 8.5 mole thiol groups/mole BR96.

Method B. On a scale >3 g, the same procedure was utilized for the DTT reaction, with the exception that the MAb solutions were de-oxygenated by bubbling with Ar. Purification after DTT reduction was accomplished by ultrafiltration in a Filtron Minisette unit. The Minisette was fitted with two Filtron 30K cassettes and was connected to a Watson Marlow 604S pump with Bioprene tubing. The MAb solution was ultrafiltered at 0° C. under Ar against Ar-bubbled PBS, pH 7.0 (eluant flow rate 100–150 ml/min., 25 psi backpressure), while continually monitoring eluant for thiol content as above. In a typical example, a 6.6 g batch of BR96 (550 ml at 75.3 uM) yielded 6.1 g reduced BR96 (800 ml at 47.6 uM MAb, 398 uM thiol) for a yield of 92% and thiol titer of 8.4 mole thiol groups/mole BR96.

Conjugation

The following procedure, for the conjugation of BR96 and 2b, is typical of that used for all linkers cited herein. (See Riddles, P. W., Blakeley, R. L., Zerner, B., (1979) Ellman's reagent: 5,5'-Dithiobis(2-nitrobenzoic acid)-A reexamination. *Anal. Biochem.*, 94, 75.) To reduced BR96 from Method A (125 ml, 6.07 umole MAb, 51.5 umole thiol) was added dropwise at 0° C. under Ar a solution of 2b (93 mg, 67.2 umole) in 5 ml Ar-bubbled H$_2$O. After stirring for 30 min., the reaction was filtered through a 0.22 u sterile filter. Conjugate was purified at 4° C. by percolation (approximately 2 ml/min.) through a 1"×36" Bio-Beads column (initially prepared by swelling and packing in methanol, then equilibrated in H$_2$O, and finally PBS, pH 7.0). The purified conjugate was filtered again through a 0.22 u sterile filter to yield 155 ml of BR96-2b (BR96, 39.13 uM; DOX, 589.0 uM; MR, 15.1 mole DOX/mole BR96; yield, 100%). Conjugate was frozen in liquid n$_2$ and stored at −80° C.

EXAMPLE 70

Biological Studies

Materials and Methods

Monoclonal Antibodies and Immunoconjugates. MAb BR64 (murine IgG$_1$) and MAb BR96 (mouse/human chimeric; human IgG1) identify Le$^y$ related tumor associated antigens expressed on carcinomas of the lung, colon, breast, and ovary. The MAbs are rapidly internalized following antigen-specific binding (Hellström, I., Garrigues, H. J., Garrigues, U. and Hellström, K. E. (1990). Highly tumor-reactive, internalizing, mouse monoclonal antibodies to Le$^y$-related cell surface antigen, *Cancer Research* 50, 2183–2190. Trail et al., 1992; Trail et al., 1993; Willner, D., Trail, P. A., Hofstead, S. J., King, H. D., Lasch, S. J., Braslawsky, G. R., Greenfield, R. S., Kaneko, T. and Firestone, R. A. (1993). (6-Maleimidocaproyl)-hydrazone of doxorubicin—a new derivative for the preparation of immunoconjugates of doxorubicin. *Bioconjugate Chem* 4, 521–527). Doxorubicin immunoconjugates of various DOX/MAb molar ratios were prepared with both chimeric BR96 and control human IgG.

Tumor Cell Lines. L2987 is a human lung line which expresses the BR64 and BR96 antigens. L2987 was obtained from I. Hellström (Bristol-Myers Squibb, Seattle, Wash.).

In vitro cytotoxicity assays. In vitro cytotoxicity assays were performed as described previously (Trail et al., 1992). Briefly, monolayer cultures of L2987 human carcinoma cells were harvested using trypsin-EDTA (GIBCO, Grand Island, N.Y.), and the cells counted and resuspended to $1 \times 10^5$/ml in RPMI-1640 containing 10% heat inactivated fetal calf serum (RPMI-10%FCS). Cells (0.1 ml/well) were added to each well of 96 well microtiter plates and incubated overnight at 37° C. in a humidified atmosphere of 5% $CO_2$. Media was removed from the plates and serial dilutions of DOX or MAb-DOX conjugates added to the wells. All dilutions were performed in quadruplicate. Cells were exposed to DOX or MAb-DOX conjugates for various times (2 h–48 h as denoted in results) at 37° C. in a humidified atmosphere of 5% $CO_2$. Plates were then centrifuged (200×g,5 min), the drug or conjugate removed, and the cells washed 3× with RPMI-10%FCS. The cells were cultured in RPMI-10%FCS (37° C., 5% $CO_2$) for an additional 48 h. At this time the cells were pulsed for 2 h with 1.0 uCi/well of [$^3$H]thymidine New England Nuclear, Boston, Mass.). The cells were harvested onto glass fiber mats (Skatron Instruments, Inc., Sterling, Va.), dried, and filter bound [$^3$H]thymidine radioactivity determined (β-Plate scintillation counter, Pharmacia LKB Biotechnology, Piscataway, N.J.). Inhibition of [$^3$H]thymidine uptake was determined by comparing the mean CPM for treated samples with that of the mean CPM of the untreated control. In studies designed to evaluate the stability of various linkers, cells were exposed to BR96 or control IgG conjugates for varying periods of time (2–48 h) and the specificity ratio (IC50 IgG-DOX/IC50 BR96-DOX) calculated for the various exposure times.

Experimental Animals. Congenitally athymic female mice of Balb/c background (Balb/c nu/nu; Harlan Sprague-Dawley, Indianapolis, Ind.) were used in thse studies. Mice were housed in Thoren caging units on sterile bedding with controlled temperature and humidity. Animals received sterile food and water ad libitum.

Human Tumor Xenograft Models. The L2987 human tumor line was established as tumor xenografts in athymic mice and maintained by serial passage as described previously (Trail et al., 1992). L2987 tumors were measured in 2 perpendicular directions at weekly or biweekly intervals using calipers. Tumor volume was calculated according to the equation: $V=1xw^2/2$ where: V=volume (mm$^3$), 1=measurement of longest axis (mm), and w=measurement of axis perpendicular to 1. In general, there were 8–10 mice per control or treatment group. Data are presented as median tumor size for control or treated groups. Antitumor activity is expressed in terms of median log cell kill (LCK): where LCK=T-C/TVDT×3.3. T-C is defined as the median time (days) for treated tumors to reach 500 mm$^3$ size minus the median time for control tumors to reach 500 mm$^3$ in size and TVDT is the time (days) for control tumors to double in volume (250–500 mm$^3$). Partial tumor regression reflects a decrease in tumor volume to ≦50% of the initial tumor volume; complete tumor regression refers to a tumor which for a period of time is not palpable; and cure is defined as an established tumor which is not palpable for a period of time ≧10 TVDT's.

Therapy. Treatments were administered by the ip or iv route on various schedules as denoted. DOX was diluted in normal saline and MAb and MAb-DOX conjugates were diluted in PBS. All therapy was administered on a mg/kg basis calculated for each animal and doses are presented as mg/kg/injection. Control animals were not treated. Doses of immunoconjugate are reported based on the drug (equivalent DOX) and antibody content. The maximum tolerated dose (MTD) for a treatment regimen is defined as the highest dose on a given schedule which resulted in <20% lethality.

Results

Relationship Between Drug/MAb Molar Ratio and In vitro Potency of Linear and Branched DOX Hydrazone Conjugates The relationship between conjugate molar ratio and the in vitro potency of DOXHZN conjugates was reported previously (Trail et al., 1992). In these studies BR64-DOXHZN (disulfide linked) conjugates were prepared with conjugate ratios ranging from 1–8. The in vitro potency of the immunoconjugates varied over a 33 fold range (IC$_{50}$ values of 1–33 uM DOX) and potency was correlated with conjugate molar ratio; conjugates of higher mole ratio were significantly ($p<0.05$) more potentin vitro on both a DOX and MAb basis than those conjugates prepared at lower mole ratios. However, the number of DOX molecules which can be directly linked to a given MAb without a subsequent reduction in MAb binding affinity is limited. For example, Shih et al., demonstrated a reduction in MAb avidity and antigen-specific potency was as molar ratios of directly linked DOX conjugates exceeded 10 (Shih, L. B., Sharkey, R. M., Primus, F. J. and Goldenber, D. M. (1988). Site-specific linkage of methotrexate to monoclonal antibodies using an intermediate carrier. *International Journal of Cancer* 41, 8320839; Shih et al., 1991). Therefore, the use of branched linkers which increase the drug/MAb molar ratio by a factor of $2^n$ (wherein n is a positive integer) without increasing the number of conjugation sites on the MAb molecule was employed.

As shown in Table 1, the conjugate molar ratios of the various singly branched conjugates (i.e., $2^n$ wherein n=1) ranged from 11–16 and that of the doubly branched conjugates (i.e., $2^n$ wherein n=2) was 24. On an individual lot basis (Table 1), the singly branched DOXHZN conjugates were 2–20 fold (IC$_{50}$ values of 0.1–1.0 uM equivalent DOX), and the doubly branched conjugates (IC50 of 0.2 uM) were 10 fold, more potent than the straight chain DOXHZN conjugate BMS-182248 (2 uM DOX). As used herein "BMS-182248" refers to the straight chain conjugate as disclosed by Trail, P. A., Willner, D., Lasch, S. J., Henderson, A. J., Hofstead, S. J., Casazza, A. M., Firestone R. A., Hellström, K. E.(1993), Cure of xenografted human carcinomas by BR96-Doxorubicin Immuno-conjugates, *Science* 261,212–215. Thus, increasing the concentration of DOX delivered per BR96 MAb, by increasing the conjugate molar ratio (M.R.) resulted in a significant increase in the in vitro potency of the conjugates. As shown in Table 2, the mean in vitro potency of various single and double branches conjugates was similar (0.2–0.5 uM DOX) and each offered an in vitro potency advantage over that of BMS-182248 on both a DOX and MAb basis.

TABLE 1

Cytotoxicity of individual lots of branched DOX hydrazone conjugates relative to BMS-182248.

| Conjugate | Example No. | Compound No. | Lot No. | M.R. | IC$_{50(uM\ DOX)}$ |
|---|---|---|---|---|---|
| BMS-182248 | | | pooled date | 8 | 2.0 |
| MC-Glu-(β-Ala-DOX)$_2$ | 29 | 3c | 33878-020 | 13.9 | 0.2 |
| MC-Glu-(DOX)$_4$ | 40 | 18c | 33878-031 | 24.0 | 0.2 |
| | | | 33878-034 | 24.4 | 0.2 |
| MB-Glu-(DOX)$_2$ | 14 | 2b | 33119-166a | 11.3 | 0.9 |
| | | | 33878-132 | 11.7 | 1.0 |
| | | | 33878-133 | 12.3 | 0.7 |
| | | | 33878-134 | 12.4 | 0.4 |
| | | | 32178-180 | 13.7 | 0.4 |
| | | | 33119-164a | 14.1 | 0.5 |
| | | | 33878-052 | 16.2 | 0.1 |
| | | | 33878-60 | 15.0 | 0.6 |
| MB-Glu-(β-Ala-DOX)$_2$ | 28 | 3b | 33878-066 | 11.6 | 0.5 |
| | | | 34616-53 | 11.9 | 0.4 |
| | | | 33878-050 | 12.1 | 0.3 |
| MC-Glu-(DOX)$_2$ | 16 | 2c | 33878-058 | 11.8 | 0.7 |
| | | | 33878-064 | 14.6 | 0.5 |
| | | | 33878-141 | 15.1 | 0.2 |
| | | | 32178-174 | 16.1 | 0.1 |
| | | | 32252-193 | 13.8 | 0.2 |
| MP-Glu(DOX)$_2$ | 13 | 2a | 33878-127 | 14.5 | 0.3 |
| | | | 32178-182 | 15.4 | 0.2 |
| | | | 33878-120 | 15.5 | 0.2 |
| | | | 33878-113 | 15.6 | 0.1 |
| MB-D-Glu(DOX)$_2$ | 15 | D-2b | 33119-191 | 15.3 | 0.2 |
| | | | 33119-197 | 11.2 | 0.2 |
| MP-Glu-(β-Ala-DOX)$_2$ | 27 | 3a | 33878-173 | 11.7 | 0.5 |

TABLE 2

In vitro potency and specificity of branched chain conjugates.

| Conjugate | Compound No. | MR (range) | IC$_{50}$(uM DOX) (Mean) | IC$_{50}$(uM MAb) (Mean) | specificity ratio[a] |
|---|---|---|---|---|---|
| BMS-182248 | | 8 | 2.0 | 0.25 | >5 |
| MC-Glu-(β-Ala-DOX)$_2$ | 3c | 14 | 0.2 | 0.01 | ND[b] |
| MC-Glu-(DOX)$_4$ | 18c | 24 | 0.2 | 0.008 | ND |
| MB-Glu-(DOX)$_2$ | 2b | 11.3–16.2 | 0.5 | 0.04 | >16 |
| MB-Glu-(β-Ala-DOX)$_2$ | 3b | 11.6–12.1 | 0.4 | 0.03 | >25 |
| MC-Glu-(DOX)$_2$ | 2c | 11.8–16.1 | 0.3 | 0.02 | 31 |
| MP-Glu-(DOX)$_2$ | 2a | 14.5–15.6 | 0.2 | 0.01 | >40 |
| MB-D-Glu-(DOX)$_2$ | D-2b | 11.2–15.3 | 0.2 | 0.02 | 35 |
| MP-Glu-(β-Ala-DOX)$_2$ | 3a | 11.7 | 0.5 | 0.04 | >20 |

[a]Secificity Ratio defined as: IC50 IgG-DOX/IC50 BR96-DOX
[b]Not determined

In vitro Stability of Singly Branched DOX Conjugates

Among the characteristics desirable for efficacous MAb-drug conjugates are linker chemistries which are extremely stable in the extracellular environment yet liberate drug efficiently upon internalization into antigen-expressing cells. One method for assessing extracellular stability, and in part, intracellular hydrolysis rates is to evaluate antigen-specific cytotoxicity of binding relative to non-binding conjugates over various exposure times. In these types of experiments, extracellular stability will be reflected by the lack of potency of non-binding immunoconjugates. Rapid intracellular hydrolysis following antigen-specific internalization will result in a high level of potency which does not change significantly with increased exposure time. Several experiments have been performed with BR96-DOX conjugates prepared with linear or branched linkers. In the following experiments, L2987 cells were exposed to the various drug conjugates for 2, 8, 24 or 48 h and the IC50 values of both BR96 (binding) and IgG (non-binding) conjugates determined. The results are presented in FIGS. 1 and 2. As shown in FIG. 1, the MCDOXHZN (BMS-182248) conjugate was less potent than the branched hydrazone, MB-Glu-(DOX)$_2$; BMS-187852, conjugate during the first 24 h of exposure. The potency of the MCDOXHZN conjugate was increased over time whereas that of the branched DOXHZN remained essentially unchanged over 48 h of exposure. These data suggest that the intracellular rates of hydrolysis for the branched DOXHZN conjugate was more rapid than that of the DOXHZN conjugate.

Figure 2:
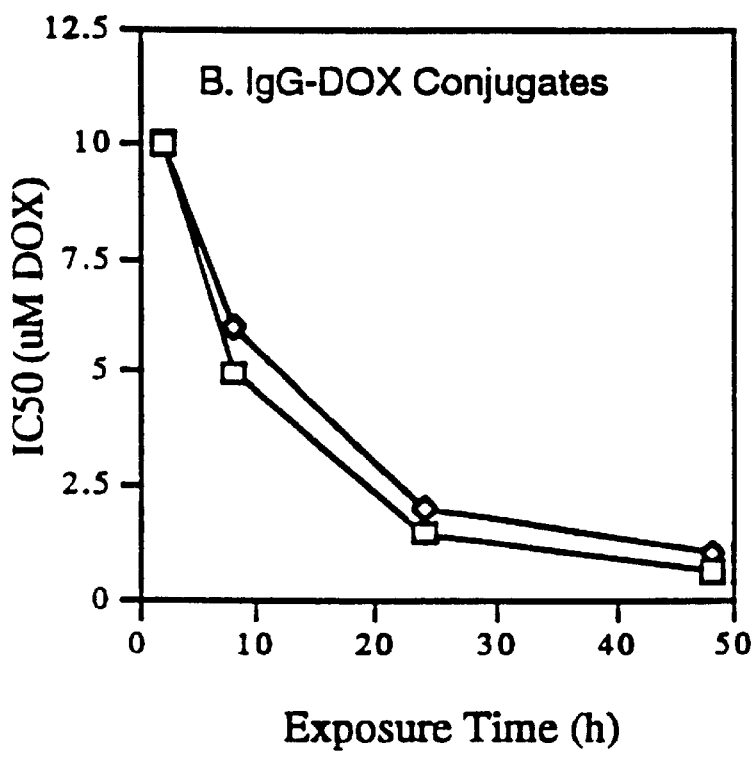
FIGS. 2—In vitro potency of IgG straight chain hydrazone and branched hydrazone conjugates following various exposure times as described in Example 62. —□— represents IgG MCDOXHZN and —◇— represents IgG MB-Glu-(DOX)$_2$.

The characteristic of extracellular stability was evaluated by examining the kinetics of cell killing of non-binding IgG conjugates prepared with the different linker chemistries. As shown in FIG. 2, the potency of both the IgG conjugates prepared as straight chain MCDOXHZN and branched chain MB-Glu-(DOX)$_2$, hydrazone conjugates increased with longer exposure times. The increase in potency of non-binding conjugates likely reflects cytotoxicity of DOX itself following release of DOX from the conjugate over time. The potency of both the linear and branched hydrazone conjugates increased in parallel, suggesting that the extracellular stability of these conjugates was quite similar. In summary, the BR96 branched hydrazone conjugates were more potent in vitro at short exposure times than were the MCDOXHZN (BMS-182248) conjugates. However, the extracellular stability of the branched conjugates was not different from that of the straight chain MCDOXHZN conjugate. Taken together, these data suggest that the branched hydrazone offers a potential advantage in the rate of intracellular release of DOX, but does not offer an increase in extracellular stability.

In Vivo Biology of Branched Chain DOX Hydrazone Conjugates

To evaluate the effect on antitumor activity of increasing the conjugate MR approximately 2 fold, BR96 and IgG conjugates were produced using six different branched linkers and the conjugates evaluated for antigen-specific activity in vivo against L2987 human tumor xenografts.

The structure and substantial purity (in particular lack of unconjugated drug) was established for each conjugate, however, unidentified impurities were present. In particular, a high MW aggregate, which is most likely a dimeric form of the conjugate was present. Therefore, antitumor activities of these branched chain conjugates were compared with that of research grade BMS-182248; (BMS-182248(RG)).

In the tables describing antitumor activity, the optimal dose of BR96-DOX conjugates is defined as the lowest dose administered which produced $\geq 4$ log cell kill and $\geq 70\%$ tumor regression. The antitumor activity of IgG-DOX conjugates at the maximum dose tested is included for demonstration of antigen-specific activity.

1. BMS-187852; MB-Glu-(DOX)$_2$

The molar ratio of the BMS-187852 conjugates varied from 13.7–15. As shown in Table 3, 3 lots of BMS-187852 were tested. The optimal dose for both BMS-187852 and BMS-182248 was 2.5 mg/kg DOX. However, because of the doubling of the molar ratio of BMS-187852, the branched conjugate was approximately 2 fold more potent than BMS-182248(RG) on a MAb basis. The antitumor activity of BMS-187852 was antigen-specific.

TABLE 3

Antitumor activity of BMS-187852; MB-Glu-(DOX)$_2$ conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 33878-060 | 15 | 2.5 | 45 | >8 | 78 | 22 |
| IgG | 33878-056 | 18 | >10 | >160 | 2.6 | 0 | 0 |
| BR96 | 32178-180 | 13.7 | 2.5 | 50 | >6 | 100 | 0 |
| IgG | 32178-178 | 15.2 | >5 | >45 | 1.7 | 0 | 0 |
| BR96 | 34616-169 | 15.1 | 2.5 | 48 | 5.8 | 90 | 10 |
| IgG | 34616-178 | 14.5 | >5 | >95 | 0 | 0 | 0 |

2. BMS-187853; MB-Glu-(β-Ala-DOX)$_2$

Two lots of BMS-187853 conjugate (molar ratios approximately 11.5) were evaluated against established L2987 lung tumor xenografts. The antitumor activity of the 2 lots was similar; both produced optimal antigen-specific antitumor activity at doses of approximately 2.0 mg/kg DOX, 45 mg/kg BR96. Overall, these conjugates were similar to BMS-182248(RG) on a DOX and 2 fold more potent on a MAb basis.

TABLE 4

Antitumor activity of BMS-187853; MB-Glu-(β-Ala-DOX)$_2$ conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 33878-066 | 11.6 | 2.5 | 44 | >6.7 | 55 | 22 |
| IgG | 33878-078 | 16.2 | >10 | >178 | 1.1 | 0 | 0 |
| BR96 | 32878-158 | 11.5 | 2.0 | 46 | 5.2 | 50 | 20 |
| IgG | 32878-162 | 13.7 | >5 | >100 | 0 | 0 | 0 |

3. BMS-188077; MC-GLU(DOX)2

The DOX/BR96 molar ratio of BMS-188077 conjugates was in the range of 14.6–16.1. As shown in Table 5, antigen-specific antitumor activity was observed for BMS-188077. BMS-188077 was of similar potency as BMS-182248(RG) on a DOX equivalent basis but due to the increase in the molar ratio, approximately 2 fold more potent on a MAb basis.

TABLE 5

Antitumor activity of BMS-188077;MC-Glu-(DOX)$_2$ conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 33878-064 | 14.6 | 2.5 | 48 | 4.6 | 30 | 70 |
| IgG | 33878-054 | 16.2 | >10 | >163 | 1.7 | 0 | 0 |
| BR96 | 32178-174 | 16.1 | 2.5 | 42 | >4 | 87.5 | 12.5 |
| IgG | 32178-176 | 12.2 | >5 | >114 | 0.7 | 0 | 0 |
| BR96 | 33878-141 | 15.1 | 2.5 | 45 | >6 | 75 | 25 |
| IgG | 33878-146 | 15.5 | >5.0 | 84 | 0.8 | 0 | 0 |

4. BMS-189099;MP-Glu-(DOX)$_2$

Three lots of BMS-189099 conjugates were evaluated in parallel with non-binding IgG conjugates (BMS-188078) produced with the same linker chemistry. The mole ratios of the BR96 conjugates were in the range of 14.5–15.5. The antitumor activity of BMS-189099 and non-binding conjugates is presented in Table 6. Antigen-specific antitumor activity was observed in vivo. The BMS-189099 conjugates were of similar potency as BMS-182248(RG) on a DOX basis but approximately 2 fold more potent on a MAb basis.

TABLE 6

Antitumor activity of BMS-189099 (MP-Glu-(DOX)$_2$) conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 33878-120 | 15.5 | 2.5 | 44 | >7.6 | 90 | 10 |
| IgG | 33878-118 | 15.9 | >5 | >79 | 0.3 | 0 | 0 |
| BR96 | 32178-182 | 15.35 | 1.25 | 23 | >6.3 | 50 | 25 |
| IgG | 32178-184 | 15.91 | >5 | >86 | 1.9 | 0 | 0 |
| BR96 | 33878-127 | 14.5 | 2.5 | 48 | >4 | 80 | 20 |
| IgG | 33878-125 | 14.7 | >5 | >95 | 0.9 | 0 | 0 |

5. BMS-189812;MB-[D]-GLU(DOX)2

The molar ratios of the BMS-189812 conjugates were in the range of 11–15 moles DOX/moles BR96. Data for the antitumor activity of BMS-189812 is summarized in Table 7. The optimal dose of BMS-189812 was approximately 2 mg/kg DOX, 50 mg/kg BR96. The potency on a DOX basis was similar to BMS-182248 (RG) and the conjugate was two fold more potent on a MAb basis.

TABLE 7

Antitumor activity of BMS-189812; MB-[D]-Glu-(DOX)$_2$ conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 33119-191 | 15.3 | 2.5 | 45 | >5 | 75 | 25 |
| IgG | 33119-189 | 18 | >5 | >89 | 0.8 | 0 | 0 |
| BR96 | 32119-197 | 11.2 | 1.0 | 27 | 5.2 | 20 | 50 |

6. BMS-190385; MB-Glu-(β-Ala-DOX)$_2$ Conjugates

The BMS-190385 conjugates demonstrated antigen-specific activity in vivo. The antitumor activity of BMS-190385 conjugates is presented in Table 8. As shown two lots of BR96-DOX conjugate are currently being evaluated against established L2987 lung xenografts. Antigen-specific antitumor activity was observed. Although the data is still developing, it appears that the optimal dose of thse conjugates is 2 mg/kg DOX, 60 mg/kg BR96. This is similar to that of BMS-182248 on a DOX basis and slightly more potent on a MAb basis.

Summary of Branched Chain DOXHZN Conjugates

The branched chain DOXHZN conjugates evaluated herein typically had molar ratios in the range of 11–15. This is 1.5–1.8 fold higher than the molar ratio typically observed for BMS-182248. all of the conjugates evaluated demonstrated antigen-specific activity both in vitro and in vivo. Among the various branched chain conjugates, there were no significant differences in either in vitro (Table 2) or in vivo (Table 9) potency. When evaluated in vitro, the branched conjugates offered an increase in potency on both a DOX and a MAb basis. This likely reflects the fact that conjugates were assayed using a 2 h exposure and as shown in FIG. 1, the branched conjugates appear to release DOX more rapidly than the straight chain MCDOXHZN conjugate following antigen-specific internalization. The dose of equivalent DOX which produced ≧4 log cell kill and ≧70% tumor regressions was the same for both the branched chain DOXHZN and single chain DOXHZN (BMS-182248) conjugates (Summarized in Table 9). However, because the molar ratio of the branched chain conjugates was increased by 1.5–1.8 fold over that of BMS-182248, these conjugates were approximately 2 fold more potent than BMS-182248 on a MAb basis.

TABLE 8

Antitumor activity of BMS-190385; MB-Glu-(β-Ala-(DOX)$_2$ conjugates against established L2987 tumors.

| Antibody | Lot# | Molar Ratio | Optimal Dose DOX | Optimal Dose Antibody | Log Cell Kill | % Tumor Regressions Complete | % Tumor Regressions Partial |
|---|---|---|---|---|---|---|---|
| BMS-182248 Research Gr. | | 8 | 2.5 | 88 | 5 | 64 | 21 |
| BR96 | 34616-24 | 11.5 | 2.0 | 60 | >4 | 60 | 40 |
| IgG | 34616-29 | 12.6 | >5.0 | >108 | 2.7 | 0 | 0 |
| B596 | 35255-2 | 12.14 | 2.5 | 56 | 5.5 | 44 | 56 |
| IgG | 33119-199 | 14.7 | >5.0 | >92 | 0.7 | 0 | 0 |

TABLE 9

Antitumor activity of optimal doses of branched chain DOXHZN conjugates against established L2987 lung tumor xenografts.

| Compound no. | Conjugate | Molar[a] Ratio | Optimal Dose[a] DOX | Optimal Dose[a] Antibody | Log Cell[a] Kill | % Tumor Regressions[a] Complete | % Tumor Regressions[a] Partial |
|---|---|---|---|---|---|---|---|
|  | BMS-182248 | 8 | 2.5 | 88 | 5 | 64 | 21 |
| 2b | MB-Glu-(DOX)$_2$ | 14.4 | 2.5 | 47.5 | >6 | 89.0 | 11.0 |
| 3b | MB-GLU-(β-Ala-DOX)$_2$ | 11.55 | 3.75 | 79.5 | >5 | 52.5 | 21.0 |
| 2c | MC-Glu-(DOX)$_2$ | 15.27 | 2.5 | 45.0 | >4 | 64.2 | 35.8 |
| 2a | MP-Glu-(DOX)$_2$ | 15.1 | 2.1 | 38.3 | >4 | 73.3 | 18.3 |
| D-2b | Mβ-[D]-Glu-(DOX)$_2$ | 13.25 | 2.25 | 50 | >5 | 47.5 | 37.5 |
| 3a | MP-Glu-(β-Ala-DOX)$_2$ | 11.82 | 2.25 | 58 | >4 | 52.0 | 48.0 |

[a]Means

We claim:

1. A linker/drug having the formula:

$$A-Q-\overset{O}{\overset{\|}{C}}-\overset{H}{\overset{|}{N}}-CH\begin{Bmatrix}(CH_2)_a-(NH)_b-\overset{O}{\overset{\|}{C}}-(W)_{\overline{m}}-NH-\overset{H}{\overset{|}{N}}-\overset{O}{\overset{\|}{C}}-\overset{H}{\overset{|}{N}}-N=Drug\\(NH)_b-\overset{}{\underset{\|}{C}}-(W)_{\overline{m}}-NH-\overset{H}{\overset{|}{N}}-\overset{}{\underset{\|}{C}}-\overset{H}{\overset{|}{N}}-N=Drug\end{Bmatrix}$$

or $$A-Q-\overset{O}{\overset{\|}{C}}-\overset{H}{\overset{|}{N}}-CH\begin{Bmatrix}(CH_2)_a-(NH)_b-\overset{O}{\overset{\|}{C}}-(W)_{\overline{m}}-NH-N=Drug\\(NH)_b-\overset{}{\underset{\|}{C}}-(W)_{\overline{m}}-NH-N=Drug\end{Bmatrix}$$

wherein:
A is a thiol acceptor;
Q is a bridging group;
b is an integer of 0 or 1;
W is a spacer moiety;
m is an integer of 0 or 1; and
a is an integer of 2, 3 or 4.

2. The linker/drug of claim 1 wherein said Drug is an anthracycline antibiotic.

3. The linker/drug of claim 2, wherein said anthracycline antibiotic is of the formula:

wherein:
$R_1$ is —CH$_3$, —CH$_2$OH, —CH$_2$OCO(CH$_2$)$_3$CH$_3$ or —CH$_2$OCOCH(OC$_2$H$_5$)$_2$;

$R_3$ is —OCH$_3$, —OH or hydrogen;
$R_4$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethyl amine or 1-cyano-2-methoxyethyl amine;
$R_5$ is —OH, —OTHP or hydrogen; and
$R_6$ is —OH or hydrogen, provided that $R_6$ is not —OH when $R_5$ is —OH or —OTHP.

4. A linker/drug of the formula wherein
a is an integer of 0, 1, 2, or 3,
n is an integer of 1 to 6,
m is an integer of 0 or 1, and
$X^5$ is an anthracycline antibiotic.

5. The linker/drug of claim 4, wherein $X^5$ is of the formula:

wherein:
$R_3$ is —OCH$_3$, —OH, or hydrogen.

6. The linker/drug of claim 5 wherein m is 0 and n is 2 or 3.

7. A linker/drug of the formula
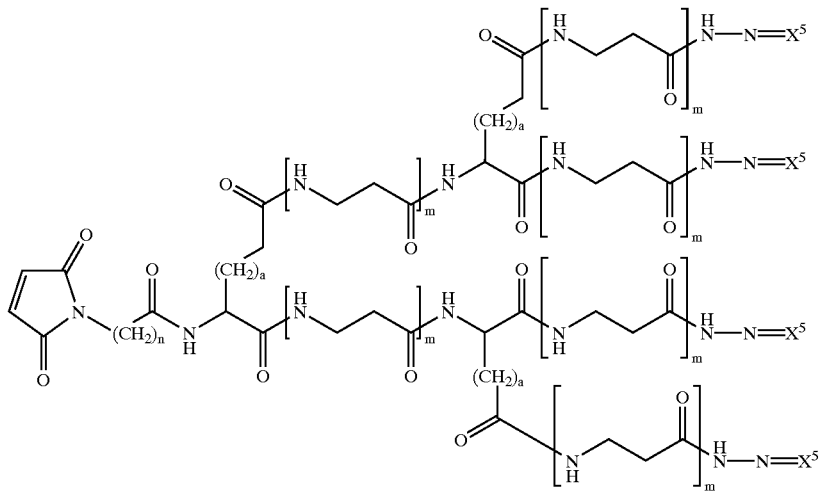
wherein
n is an integer of 1 to 6:
a is an integer of 0, 1, 2, or 3,
m is an integer of 0 or 1, and
$X^5$ is an anthracycline antibiotic.
8. The linker/drug of claim 7, wherein $X^5$ is of the formula:
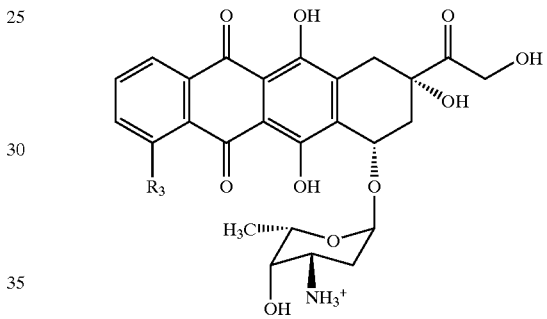
wherein
$R_3$ is —$OCH_3$, —OH, or hydrogen.
9. The linker/drug of claim 8 wherein m is 0 and n is 2 or 3.